US011648167B2

(12) United States Patent
Cooke et al.

(10) Patent No.: US 11,648,167 B2
(45) Date of Patent: May 16, 2023

(54) ADJUSTABLE CRADLE ASSEMBLY

(71) Applicant: Monteris Medical Corporation, Plymouth, MN (US)

(72) Inventors: Simon Cooke, Winnipeg (CA); Mark A. Grant, Winnipeg (CA)

(73) Assignee: Monteris Medical Corporation, Plymouth, MN (US)

( * ) Notice: Subject to any disclaimer, the term of this patent is extended or adjusted under 35 U.S.C. 154(b) by 1090 days.

(21) Appl. No.: 16/092,266

(22) PCT Filed: Apr. 14, 2017

(86) PCT No.: PCT/US2017/027814
§ 371 (c)(1),
(2) Date: Oct. 9, 2018

(87) PCT Pub. No.: WO2017/181150
PCT Pub. Date: Oct. 19, 2017

(65) Prior Publication Data
US 2020/0345572 A1    Nov. 5, 2020

Related U.S. Application Data

(60) Provisional application No. 62/323,327, filed on Apr. 15, 2016.

(51) Int. Cl.
*A61G 13/12* (2006.01)
*A61B 90/00* (2016.01)
(Continued)

(52) U.S. Cl.
CPC ............ *A61G 13/121* (2013.01); *A61B 5/055* (2013.01); *A61B 90/06* (2016.02); *A61B 90/14* (2016.02);
(Continued)

(58) Field of Classification Search
USPC .......... 602/17; 128/97, 857; 248/118, 230.6, 248/231.71
See application file for complete search history.

(56) References Cited

U.S. PATENT DOCUMENTS 3,572,835 A * 3/1971 Kees, Jr. ................ A61G 13/12
5/640
3,622,233 A * 11/1971 Blood .................. A61B 3/0083
297/391
(Continued)

FOREIGN PATENT DOCUMENTS

CN    104254296 A    12/2014
DE    10134031 A1    2/2003
(Continued)

OTHER PUBLICATIONS

Office Action and Search Report dated Sep. 17, 2020, issued in related Chinese Patent Application No. 201780023857.7, 6 pages.
(Continued)

*Primary Examiner* — Alfred J Wujciak
(74) *Attorney, Agent, or Firm* — Fox Rothschild LLP

(57) ABSTRACT

In an illustrative embodiment, an adjustable cradle assembly for adjusting a head position of a patient relative to a patient platform includes a base portion with a pair of vertical support members and a cradle portion. The vertical support members may each include at least one position aperture for setting a vertical height of the cradle portion relative to the base portion. The cradle portion may include a channel for receiving a head fixation ring. The cradle portion may include at least one set of adjustment connection points for aligning with position apertures of each vertical support member. The cradle may be pivotably connected to the vertical support members such that a pitch angle of a head position of a patient secured in the head fixation apparatus
(Continued)

may be adjusted. A set of adjustment mechanisms may releasably secure the cradle to the base at a selected lateral and/or pitch position.

10 Claims, 15 Drawing Sheets

(51) Int. Cl.
- *A61B 90/14* (2016.01)
- *F16M 11/10* (2006.01)
- *A61B 5/055* (2006.01)
- *A61B 90/10* (2016.01)

(52) U.S. Cl.
CPC ........ *F16M 11/10* (2013.01); *A61B 2090/067* (2016.02); *A61B 2090/101* (2016.02); *F16M 2200/021* (2013.01)

(56) References Cited

U.S. PATENT DOCUMENTS

| | | | |
|---|---|---|---|
| 4,033,339 A | 7/1977 | Roberts et al. | |
| 4,463,758 A * | 8/1984 | Patil | A61B 90/11 378/162 |
| 6,179,846 B1 * | 1/2001 | McFadden | A61B 90/14 606/130 |
| 7,117,551 B1 * | 10/2006 | Dinkler, II | A61B 90/14 5/643 |
| 7,450,985 B2 | 11/2008 | Meloy | |
| 7,467,004 B2 | 12/2008 | Calderon et al. | |
| 7,706,858 B1 | 4/2010 | Green et al. | |
| 9,433,383 B2 * | 9/2016 | Andrews | A61B 5/702 |
| 2006/0293589 A1 | 12/2006 | Calderon et al. | |
| 2007/0061972 A1 | 3/2007 | Brown et al. | |
| 2007/0270683 A1 | 11/2007 | Meloy | |
| 2008/0072381 A1 * | 3/2008 | Rolfes | A61B 90/14 5/637 |
| 2015/0265216 A1 | 9/2015 | Andrews et al. | |
| 2019/0053871 A1 * | 2/2019 | Moosmann | A61G 13/127 |
| 2021/0015580 A1 * | 1/2021 | Schuele | A61B 90/14 |

FOREIGN PATENT DOCUMENTS

| | | |
|---|---|---|
| WO | WO-03005922 A1 | 1/2003 |
| WO | WO-2015109086 A1 | 7/2015 |

OTHER PUBLICATIONS

Extended European Search Report dated Sep. 26, 2019, issued by the European Patent Office in related EP Application No. 17783338. 1, 9 pages.

International Search Report and Written Opinion, issued by the ISA/United States Receiving Office, regarding coresponding international patent application Serial No. PCT/US2017/027814, dated Jun. 26, 2017, 7 pages.

* cited by examiner knob A knob B knob C knob D knob E

ADJUSTABLE CRADLE ASSEMBLY

CROSS REFERENCE TO RELATED APPLICATIONS

This application is a U.S. national stage application of International application Serial No.: PCT/US2017/027814, filed on Apr. 14, 2017, which claims priority to U.S. Provisional application Ser. No. 62/323,327, filed on Apr. 15, 2016, the entireties of which are hereby incorporated by reference.

RELATED APPLICATIONS

This application claims priority to U.S. Provisional Patent Application Ser. No. 62/323,327, entitled "Adjustable Cradle Assembly," filed Apr. 15, 2016.

This application incorporates by reference, in their entirety, the following prior patent by Andrews et al. directed to image guided therapy of a tissue: U.S. Pat. No. 9,433,383, entitled "Image-Guided Therapy of a Tissue," filed Mar. 18, 2015, and prior patent by Tyc et al. directed to trajectory planning: U.S. Pat. No. 9,211,157 entitled "Probe Driver," filed Dec. 1, 2014. All above identified applications are hereby incorporated by reference in their entireties.

BACKGROUND

One well known treatment for cancerous brain tumors is surgery. In particular, surgery involves a craniotomy (i.e., removal of a portion of the skull), dissection, and total or partial tumor resection. The objectives of surgery include removal or lessening of the number of active malignant cells within the brain, and a reduction in the pain or functional impairment due to the effect of the tumor on adjacent brain structures. However, by its very nature, surgery is highly invasive and risky. Furthermore, for some tumors surgery is often only partially effective. In other tumors, the surgery itself may not be feasible, it may risk impairment to the patient, it may not be tolerable by the patient, and/or it may involve significant cost and recovery.

Another well-known treatment for cancerous brain tumors is stereotactic radiosurgery (SRS). In particular, SRS is a treatment method by which multiple intersecting beams of radiation are directed at the tumor such that the point of intersection of the beams receives a lethal dose of radiation, while tissue in the path of any single beam remains unharmed. SRS is non-invasive and is typically performed as a single outpatient procedure. However, confirmation that the tumor has been killed or neutralized is often not possible for several months post-treatment. Furthermore, in situations where high doses of radiation may be required to kill a tumor, such as in the case of multiple or recurring tumors, it is common for the patient to reach the "toxic threshold" prior to killing all of the tumors, where further radiation is inadvisable.

More recently, the treatment of tumors by "heat" (also referred to as hyperthermia or thermal therapy) has been developed. In particular, it is known that above 57° C. all living tissue is almost immediately and irreparably damaged and killed through a process called coagulation necrosis or ablation. Malignant tumors, because of their high vascularization and altered DNA, are more susceptible to heat-induced damage than normal tissue. Various types of energy sources may be used, such as laser, microwave, radiofrequency, electric, and ultrasound sources. Depending upon the application and the technology, the heat source may be extracorporeal (i.e., outside the body), extrastitial (i.e., outside the tumor), or interstitial (i.e., inside the tumor).

It is known that the location of tumors and other lesions to be excised can be determined using a magnetic resonance imaging system. Although these imaging systems have been helpful to assist the surgeon in determining a location of the tumor to be excised, use of the imaging systems ended once the location of the tumor was mapped out for the surgeon. In particular, previous excision procedures required the removal of the patient from the imaging system prior to commencing treatment. However, movement of the patient, together with the partial excision or coagulation of some of the tissue, can significantly change the location of the tumor to be excised. As a result, any possibility of providing controlled accuracy in the excision is eliminated.

There is a need for an apparatus that allows the physician to precisely fix a position of the patient's head while at the same time avoiding interference with the trajectory guide instrument that is typically used to guide the treatment probe into the tumor mass. Therefore, a heretofore unaddressed need exists to establish a head fixation device that is capable of precisely fixing the position of the patient's head to allow unobstructed access to the point of entry into the patient's head regardless of where that point of entry lies.

SUMMARY OF ILLUSTRATIVE EMBODIMENTS

The forgoing general description of the illustrative implementations and the following detailed description thereof are merely exemplary aspects of the teachings of this disclosure, and are not restrictive.

In certain embodiments, an adjustable cradle assembly for adjusting a head fixation apparatus relative to a patient platform may include a base with a pair of tabs each include a position slot for setting a vertical height relative to the platform. A cradle can be aligned between the pair of tabs and includes a channel that receives a head fixation ring. The cradle may also include at least one set of adjustment connection points that can align with the at least one position slot of a corresponding tab. A set of adjustment mechanisms may releasably connect to a respective adjustment connection point of the cradle through a selected position slot of the respective tab to lock the cradle to the base at a selected lock position. A pitch angle of a head position of a patient secured in the head fixation ring may be adjustable relative to the platform based upon the selected lock position. The adjustable cradle assembly may be used with a platform for stereotactic surgery and medical imaging and allows multiple degrees of freedom of adjustment of an angular head position of a patient that is secured in a head fixation ring relative to the platform.

In certain embodiments, after a patient is sedated, and a trajectory planning procedure is completed, a mini frame and/or the head fixation ring can be attached to the patient's head. The head fixation ring can be secured to the adjustable cradle assembly that is secured to a patient platform in an operating room where the trajectory planning procedure is conducted.

Benefits of the embodiments described herein include allowing a position of the patient's head to be precisely fixed at a particular position on a platform and at particular pitch and roll angles within the cradle assembly while at the same time avoiding interference with a trajectory instrument that may be used to guide a treatment probe into a treatment volume, such as a tumor mass.

Benefits of the embodiments described herein also include providing the ability to remotely adjust a pitch angle of a cradle of the adjustable cradle assembly and therefore a pitch angle of the patient's head that is connected to the cradle assembly through a computing system that includes a controller configured to issue control signals to actuators disposed on or near adjustment mechanisms for the cradle assembly. In addition, various sensors may be disposed on or within components of the cradle assembly that allow the position and/or angular orientation of the cradle of the cradle assembly to be automatically determined by the controller based on position and angular orientation data obtained by the sensors, and the controller may issue control signals to the actuators for the adjustment mechanisms to adjust a lateral position of a base or a pitch angle of a cradle based on the received sensor data.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings.

DETAILED DESCRIPTION OF ILLUSTRATIVE EMBODIMENTS

Figure 1A:
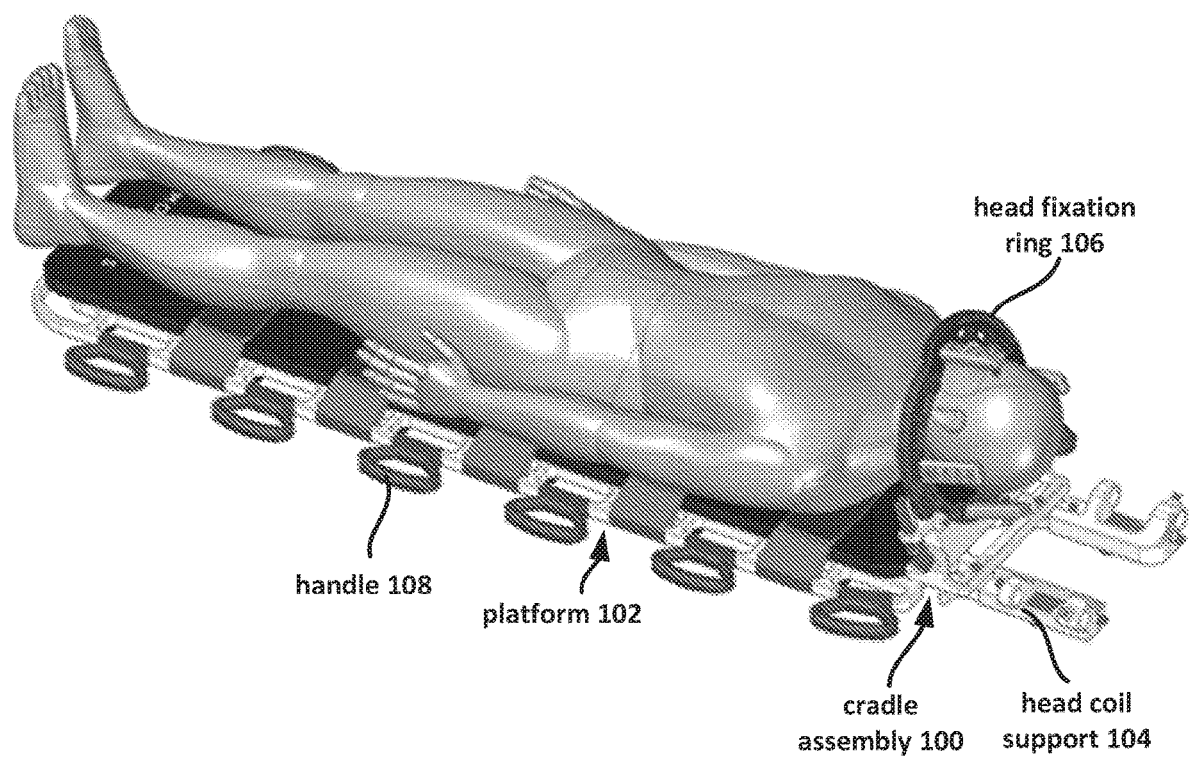
FIG. 1A illustrates a perspective drawing of a cradle assembly attached to a platform, a head coil support, and a head fixation ring.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

Aspects of the present disclosure may be directed to an adjustable cradle assembly for allowing multiple degrees of freedom for adjustment of an angular head position of a patient that is secured in a head fixation ring relative to a platform. Using an adjustment mechanism of the cradle assembly, at least one of a roll and a pitch angle of the patient's head can be adjusted, thereby creating an adjusted position. In an example, the cradle assembly includes a base, a cradle having a channel configured to receive the head fixation ring, and a set of adjustment mechanisms that allow for adjustment of a roll, a pitch angle, a lateral position, a longitudinal position, and a vertical position of the head fixation ring relative to the platform. The adjustable cradle assembly may be configured to be used with a platform used in stereotactic surgery such as radiosurgery and in medical imaging such as in magnetic resonance imaging (MRI).

Figure 4A:
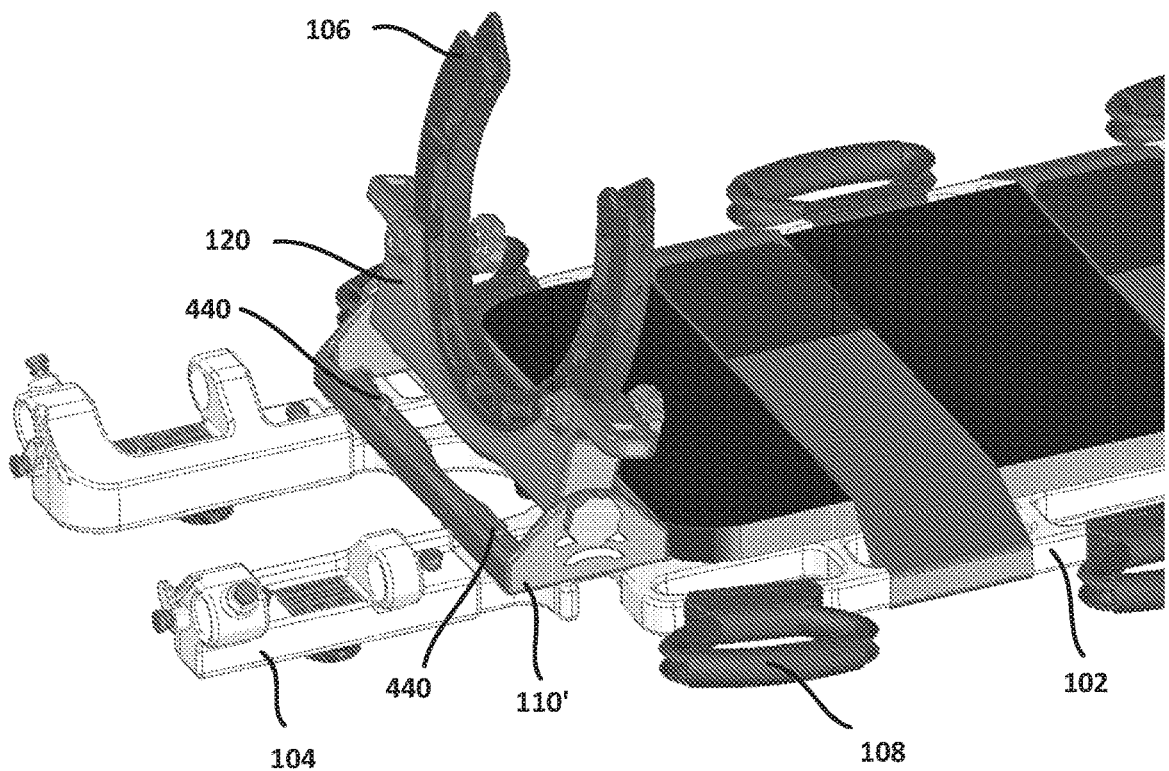
FIG. 4A is a perspective illustration of the cradle assembly attached to the platform, the head coil support, and the head fixation ring.
Figure 4B:
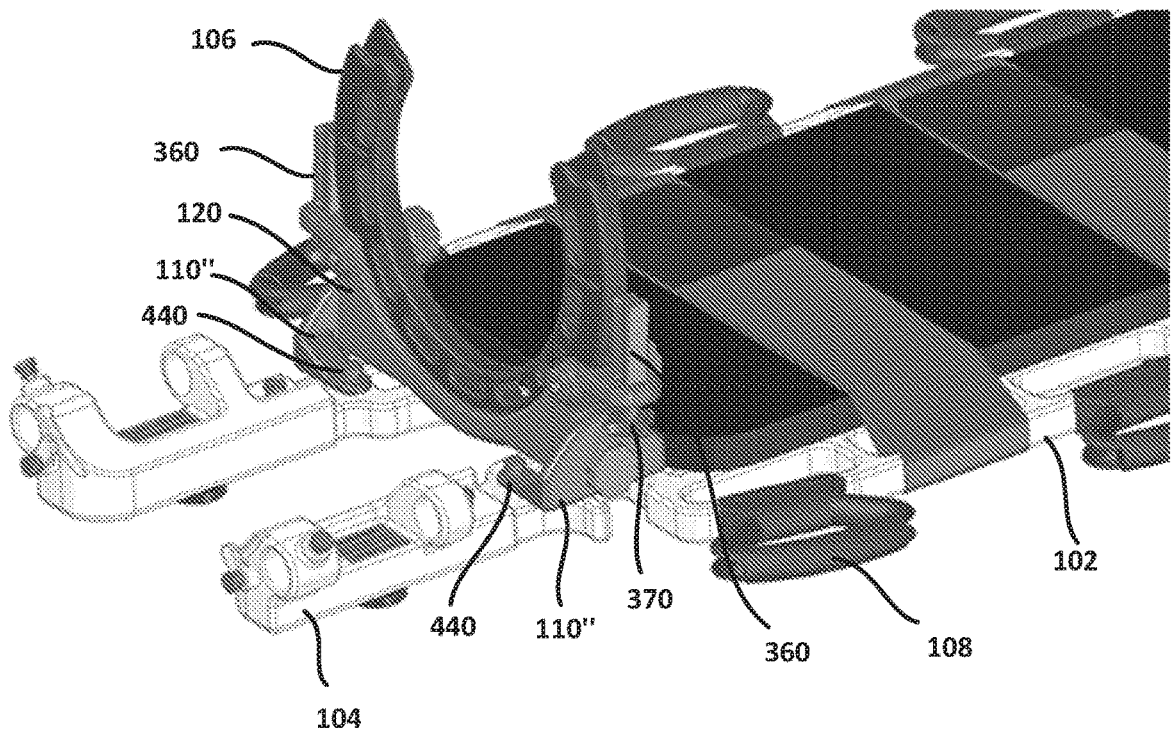
FIG. 4B is a perspective illustration of the cradle assembly attached to the platform, the head coil support, and the head fixation ring.

Turning to the figures, FIG. 1A is a perspective drawing of a cradle assembly 100 attached to a platform 102 and releasably retaining a head fixation ring 106 according to an example. A set of adjustment mechanisms 130 and 140 are configured to lock the head fixation ring 106 in the cradle assembly 100 in a set of incremental angle adjustments according to an example. In one example, the cradle assembly 100 can be attached to either the platform 102 or to a head coil support 104 using a set of adjustment mechanisms 440 as shown in FIGS. 4A and 4B. In another example, the cradle assembly 100 can be attached to both the platform 102 and the head coil support 104 using the set of adjustment mechanisms 440. In another example, the platform 102 can be considered to include the head coil support 104, as well as a set of handles 108. The platform 102 can be configured to adapt and connect to various different tables, such as an operating table and a diagnostic table including varying MRI tables provided with different MRI machines. For example, a patient may be positioned upon the platform 102 and partially restrained by the cradle assembly 100, wheeled to a surgical room or imaging room, then transferred, using the handles 108, to the operating table or diagnostic table. Alternatively, the patient may be positioned on a bed or a table connected to or including the cradle assembly 100.

Figure 5A:
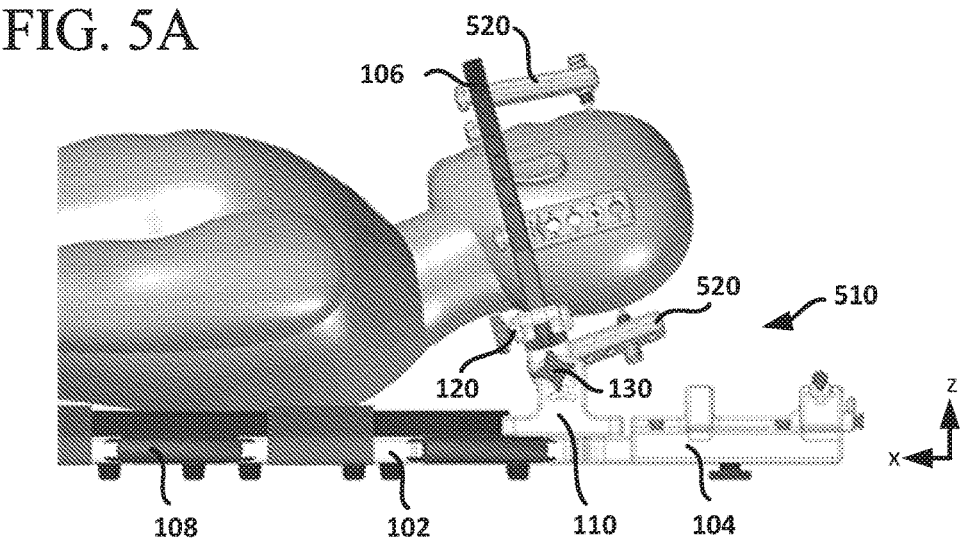
FIGS. 5A-5C illustrate a series of drawings in a y-plane demonstrating a pitch adjustment of the cradle assembly relative to the platform and the head coil support.
Figure 5B:
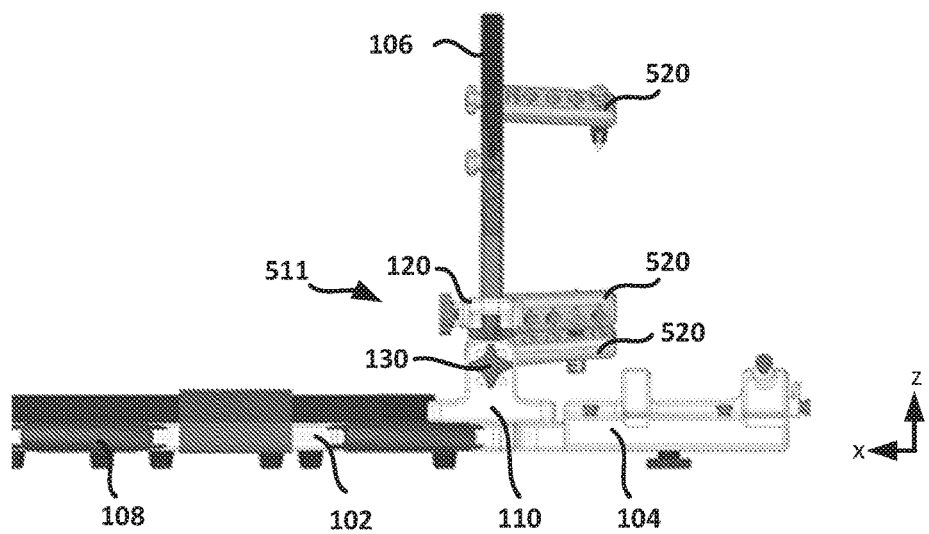
Figure 5C:
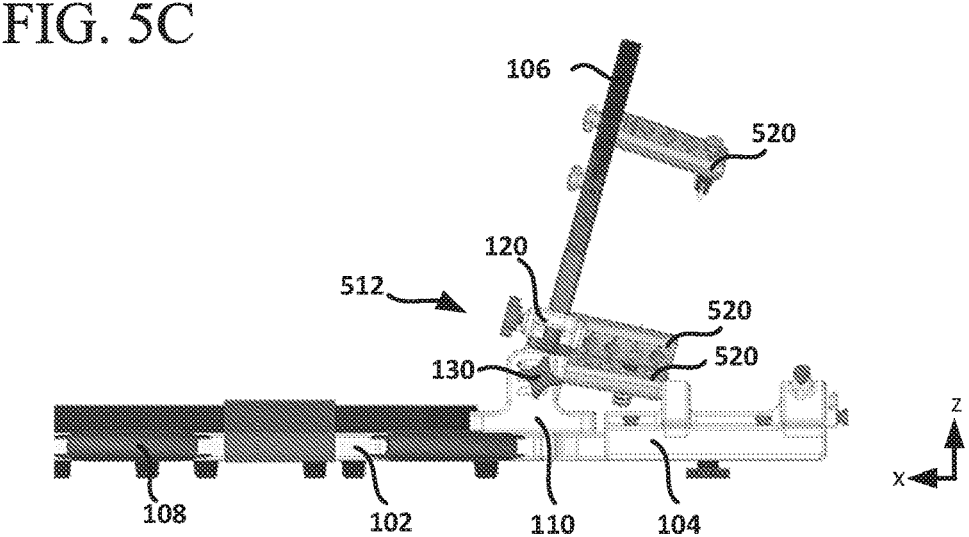

In some embodiments, the cradle assembly 100 is used in performing medical imaging, such as MRI. A head coil such as an MRI coil (not pictured) can be fixed to the head fixation ring 106 and/or the head coil support 104. FIGS. 5A-5C provide illustrative examples demonstrating a pitch adjustment in the y-plane of the cradle assembly 100, which creates different pitch angles between the head fixation ring 106 relative to the platform 102 and the head coil support 104 according to an example. Additional details describing different examples of the cradle assembly 100 are provided below.

In some implementations, cradle assembly 100 includes a base 110, a cradle 120, and a set of adjustment mechanisms 130 and 140 according to one example. In some examples, adjustment mechanisms 140 are configured to adjust the positioning of the head fixation ring 106 within the cradle 120 and lock the head fixation ring 106 within the cradle 120. In addition, the adjustment mechanisms 130 may be used to adjust a vertical position of the cradle 120 within the base 110 as well as an angular orientation of the cradle 120 within the base 110, which may correspond to a pitch angle of a patient's head within the cradle assembly 100. The base 110 can be a single piece or base 110', as illustrated in FIGS. 1B, 2A, 2B, and 4A. Alternatively, the base 110 can be divided into more than one piece or bracket section 110", as illustrated in FIGS. 1C, 2C, 2D, and 4B.

Figure 1B:
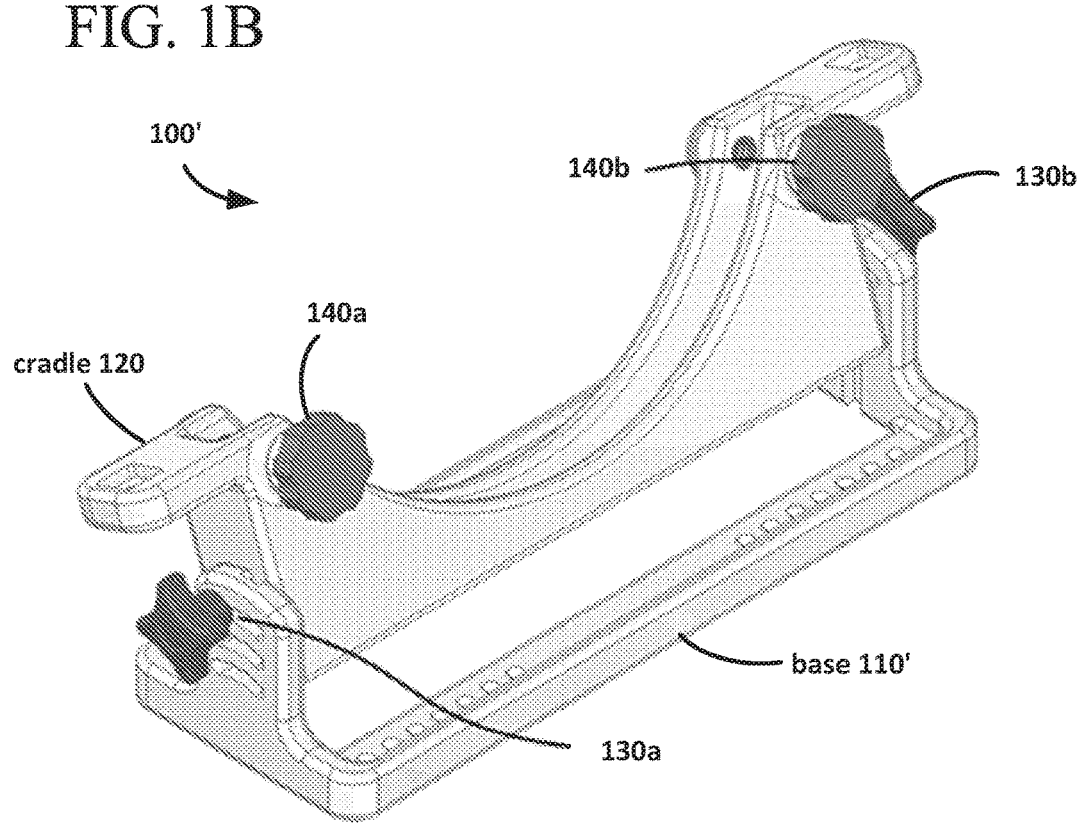
FIG. 1B illustrates a cradle assembly including a base, a cradle, and a set of adjustment mechanisms.
Figure 1C:
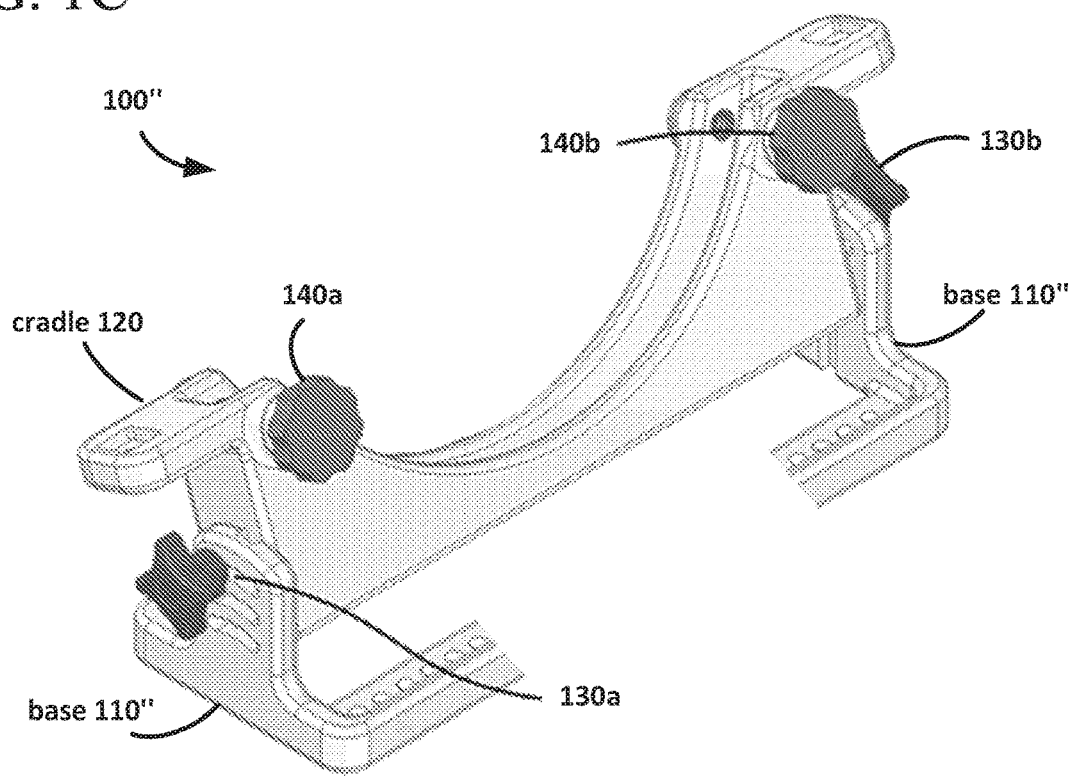
FIG. 1C illustrates a cradle assembly including a two-piece base, the cradle, and the set of adjustment mechanisms.
Figure 2A:
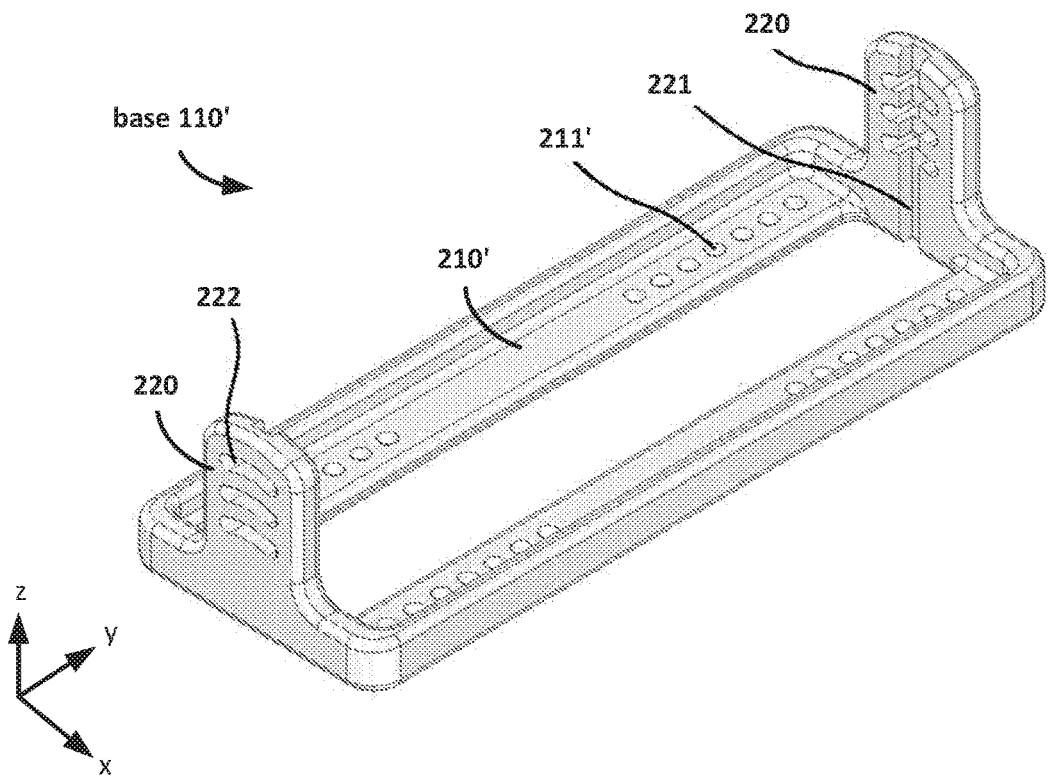
FIGS. 2A and 2B illustrate a perspective view of the base for the cradle assembly.
Figure 2C:
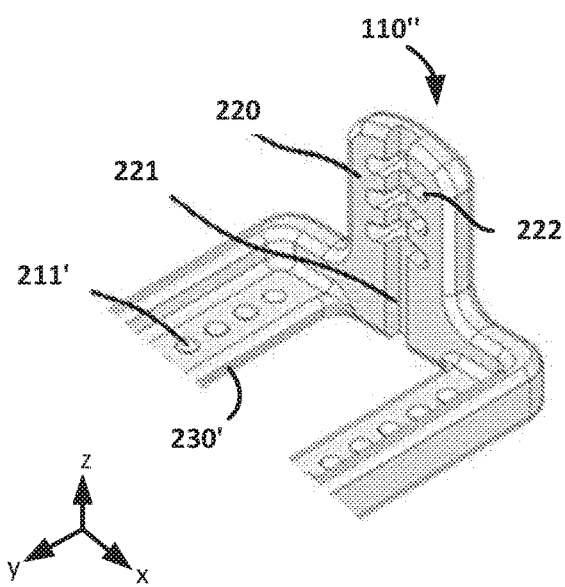
FIGS. 2C and 2D illustrate a perspective view of a two-piece base for a cradle assembly.
Figure 3A:
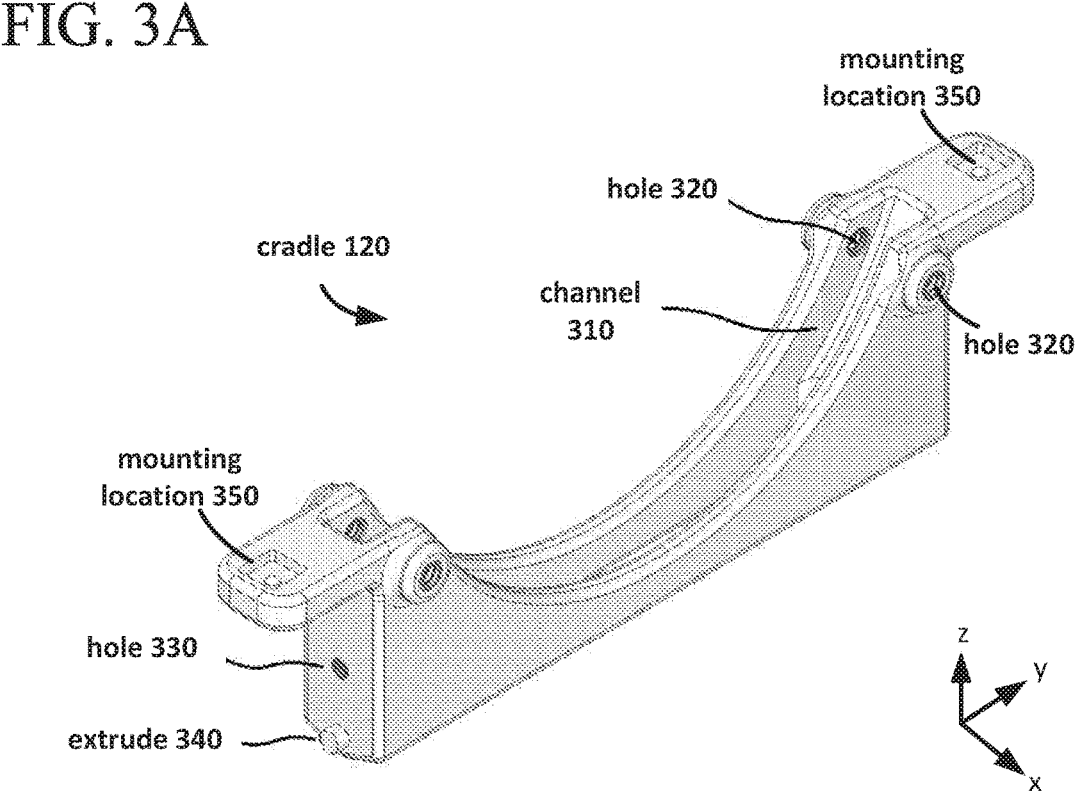
FIG. 3A illustrates a perspective view of the cradle including a pair of extrudes.

FIG. 1B shows a cradle assembly 100' including the base 110' as shown in FIG. 2A, a cradle 120 as shown in FIG. 3A, and a set of adjustment mechanisms 130 and 140 according to one example. FIG. 1C shows a cradle assembly 100" including the base 110" as shown in FIG. 2C, the cradle 120 as shown in FIG. 3A, and a set of adjustment mechanisms 130 and 140 according to one example. The base 110" can be used with a cradle assembly 100 having a different width according to one example. The base 110" can be in two identical pieces negating an opportunity for a backwards installation.

Figure 1D:
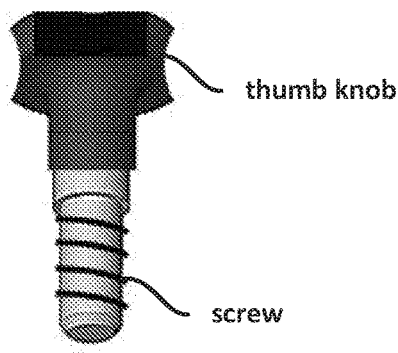
FIG. 1D illustrates different types of adjustment mechanisms for the cradle assembly.
Figure 1D:
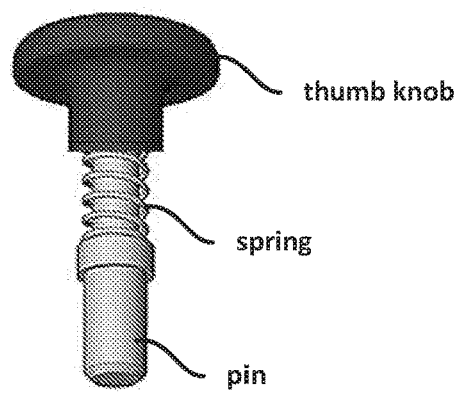
Figure 1D:
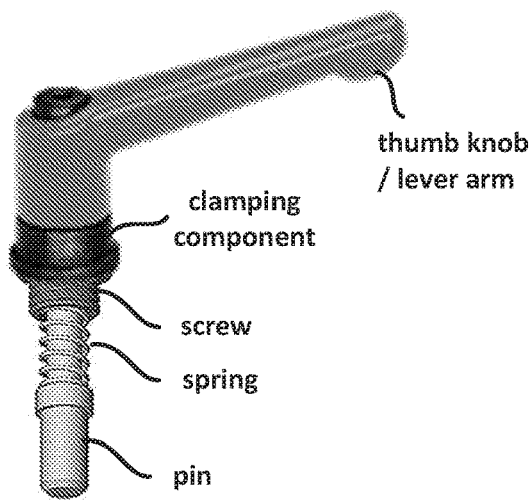
Figure 1D:
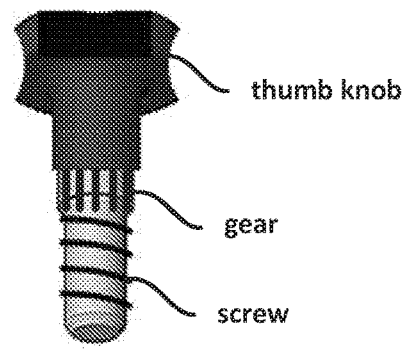
Figure 1D:
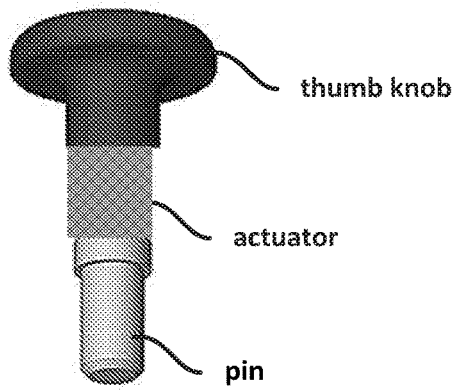

The adjustment mechanisms 130 are configured to releasably lock the base 110 and the cradle 120 together at a selected pitch angle. The adjustment mechanisms 130 can be a set of knobs such as a knob 130a, 130b. Other example adjustment mechanisms are illustrated in FIG. 1D. As illustrated, on each side of the base 110, the knob 130a, 130b can be selectively inserted in one of a vertical series of position slots 222. By positioning the knobs 130a, 130b at a selected horizontal position along a particular position slot 222, (various styles of position slots illustrated in FIGS. 2A, 2C and 2E), the pitch angle of the patient's head can be adjusted (e.g. towards the platform, FIG. 5A; centered, FIG. 5B; or away from the platform, FIG. 5C), thereby creating an adjusted position. Selection of a particular position slot 222, for example, sets a height of the cradle 120 in relation to the base 110. In some implementations, each position slot 222 is separated from another position slot 222 by a particular distance (e.g., 5 mm, 10 mm, etc.) such that an operator, upon adjusting the cradle assembly 100', may adjust the vertical position of the cradle 120 with precision.

A set of adjustment mechanisms 140 are configured to lock the head fixation ring 106 in the cradle 120 according to an example as shown in FIGS. 4A and 4B. The adjustment mechanisms 140, as illustrated, can include a pair of knobs 140a (only one shown from this perspective) at one end of a channel 310 as shown in FIGS. 3A and 3B, and a pair of knobs 140b at the other end of the channel 310 to lock the head fixation ring 106 in the cradle 120 according to an example. Although FIGS. 1B and 1C are illustrated using particular styles of adjustment mechanisms, in further embodiments, other adjustment mechanisms may be used with the illustrated base 110' or alternative base 110" described, for example, in relation to FIGS. 2C and 2D.

In an example, returning to FIG. 1A, the cradle assembly 100 may include various sensors configured to detect orientation angles of components of the cradle assembly 100, and in effect the head fixation ring 106, relative to the base 110 and/or platform 102. The sensors can be electrical sensors, optical sensors such as in a sundial and/or a mechanical sensor such as a level having a bubble in a fluid. The sensors may also include a combination of one or more types of the sensors, such as an optical detection of the mechanical sensor. In some examples, the sensors may also include acceleration and/or position sensors disposed on or within various components of the cradle assembly 100 and head fixation ring 106 that are configured to detect an adjustment angle of the cradle assembly 100 relative to the platform 102 as well as differences between angular orientations of a cradle 120 and head fixation ring 106 that may indicate that the head fixation ring 106 has not been seated properly within the cradle 120. For example, when the patient's head is seated properly within the cradle 120, the angular orientations of the cradle 120 and head fixation ring 106 relative to the base 110 and/or platform 102 may be substantially equal, and differences in the angular orientations of the cradle 120 and head fixation ring 106 by more than a threshold amount may indicate that the head fixation ring 106 is not seated properly within the cradle 120 and may require reseating.

In some implementations, the acceleration and/or position sensors may include any combination of multi-axis accelerometers, gyroscopes, and magnetometers. In some implementations, accelerometers may be configured measure an amount of acceleration in a particular direction, gyroscopes may be configured to measure changes in orientation or relative velocity, and magnetometers measure changes in magnetic fields that can be used to determine absolute orientation of the elements to which the magnetometers are connected. Because accelerometers, gyroscopes, and magnetometers may be used to measure different features of inertial movement, the sensors may be combined into a single inertial measurement unit (IMU). In one example, gyroscope sensors may be disposed at one or more locations on or within the cradle 120 and/or fixation ring 106 that detect changes in the orientation angles of the cradle 120 and/or fixation ring 106, which may occur when the patient is being placed on the platform 102, due to improper tightening of the adjustment mechanisms 130, 140 within the cradle assembly 100.

The position sensor(s), in some examples, may be a flex sensor or potentiometer providing electrical resistance correlating to a hinge position. For example, the signal of a flex sensor or potentiometer may correspond to an amount of deflection or bending of the sensor based upon the current state of the cradle relative to the base. The flex sensor may be installed, for example, between the cradle 120 and the base 110 so that it flexes like a stick of gum while the cradle is angled relative to the base 110. In its downward most position (e.g., closest to horizontal positioning achievable by the cradle 120), the resistance in the flex sensor will be at its greatest, issuing the strongest position signal. In another example, the position sensor may be a rotary encoder built into the positioning knob 130 and configured to recognize relative rotational positioning of the cradle 120. For example, a rotary encoder may be an absolute encoder identifying a particular angle which corresponds to the angle between the cradle 120 and the base 110.

In illustrative examples shown in FIGS. 5A-5C, the sensors disposed on or within the platform 102, base 110, cradle 120, and/or head fixation ring 106 can be used to determine a pitch angle of the head fixation ring 106 and/or cradle 102 relative to the platform 102 and/or base 110. For example, FIG. 5A shows an obtuse pitch angle 510 between the head fixation ring 106/cradle 120 and an upper end of the platform 102 (e.g., an end of the platform 102 extending away from the head and body of the patient or the end of the platform 102 on which the cradle assembly 100 is configured) such that the patient's head is tilted toward the patient's chest. FIG. 5B shows a pitch angle 511 between the head fixation ring 106/cradle 120 and the upper end of the platform 102 that is approximately at a right angle such that the cradle 120 and/or head fixation ring 106 are substantially perpendicular to the platform 102. In addition, FIG. 5C shows an acute pitch angle 512 between the head fixation ring 106/cradle 120 and the upper end of the platform 102 such that the patient's head is tilted away from the patient's chest.

Referring back to FIGS. 1A-1C, in some examples, the detected pitch angle by the sensors can be used for either manual or remote, automatic angular adjustment of the cradle 120 and/or head fixation ring 106 within the cradle assembly 100. For example, during manual adjustment of the pitch angle, the computer workstation of the computing system may be configured to output audible and/or visual notifications to a user, such as a medical practitioner configuring the cradle assembly 100 on the platform 102 so that the user can fix the cradle 102 at a predetermined pitch (orientation) angle. Examples of notifications include audible or visual read-outs of the orientation angle of the cradle 102 and/or head fixation ring 106 and/or an audible or visual indication that the orientation angle has reached a predetermined orientation angle set point.

In some examples, the cradle assembly 100 may include fiducial markers disposed on one or more surfaces of the base 110, cradle 120, and/or head fixation ring 106 that can be used in conjunction with one or more imaging devices, such as cameras or the MRI imaging system, to determine the orientation angles of the cradle 120 and/or head fixation ring 106 relative to base 110 and/or platform 100. For example, the fiducial markers may be disposed on a bottom surface of the cradle 120 such that an imaging device that is proximate or attached to the base 110 and directed upward toward the cradle 120 may be able to detect the fiducial markers within the captured images. In some implementations, the relative orientation angle of the cradle 120 relative to the base 110 can be determined based on the amount of visibility and/or detected features of the fiducial markers in images captured by the imaging devices.

In some implementations, one or more of the sensors may be removable prior to operating to reduce potential interference with MRI imaging. For example, a camera system for ensuring positioning base upon fiducial markers or other recognizable markings may be removed prior to moving the patient within the MRI bore.

In some examples, the sensors disposed on or within the platform 102, base 110, cradle 120, and/or head fixation ring 106 may be communicatively coupled to a computing system including a controller 820 (FIG. 8) that can be used to automatically determine the orientation angle of the cradle 120 and/or head fixation ring 106 based on sensor data received from the sensors of the cradle assembly 100. The sensors may be communicatively coupled to the controller 820 that is remote from the cradle assembly 100 through a combination of wired and wireless communication networks. For example, the computing system may include a computer workstation in an MRI or operating room that can be used to remotely adjust the orientation of the cradle 120 and/or fixation ring 106 within the cradle assembly 120 based on the received sensor data.

In some examples, the controller 820 may determine that the head fixation ring 106 is not seated properly within the cradle 120 and may require reseating based on differences in the angular orientations of the cradle 120 and head fixation ring 106 by more than a threshold amount. In some implementations where the cradle assembly 100 may include fiducial markers disposed on one or more surfaces of the base 110, cradle 120, and/or head fixation ring 106 in addition to imaging devices configured to capture images of the cradle assembly 100 with the fiducial markers, the imaging devices may be communicatively coupled to the controller 820, which can use the captured images to determine the orientation angle of the cradle 120 and/or head fixation ring 106 based on detected features of the fiducial markers in the images. In addition, in implementations where the adjustment mechanisms 130, 140 can be remotely and/or automatically adjusted via an interface at the computer workstation, the orientation angle sensor data received from the sensors disposed on or within the platform 102, base 110, cradle 120, and/or head fixation ring 106 can be used to determine amounts of adjustment of the adjustment mechanisms 130, 140. In some implementations, the orientation angle of the cradle 120 may be remotely adjusted based on the received sensor data while the patient's head is attached to the cradle assembly 100 via the head fixation ring 106.

In some implementations, the wireless communication networks may include short-range wireless communication network, such as a Wi-Fi, Bluetooth, Zigbee, or Ultra Wide Band (UWB) network. For example, the sensors and controller 820 may each include wireless communication circuitry, such as a radio, transceiver, and other associated circuitry, that allow the sensors and controller 820 to communicate via the wireless communication network. The type of wireless communication technology that is used for the implementations described herein can be based on various factors that can include battery life, data usage, security and/or line-of-sight restrictions, and other concerns. In some embodiments, ZigBee or Bluetooth wireless communications may be used in applications where link security is prioritized. In other embodiments where frequency interference is a concern, Bluetooth or UWB communications may be used since both technologies use adaptive frequency hopping to avoid channel collision. In embodiments where a total of frequency channels is prioritized, Bluetooth wireless communications may be used.

Turning to FIG. 1D, different types of adjustment mechanisms that can be implemented in the cradle assembly 100 are illustrated. In an example, each adjustment mechanism 130 and 140 can have the same or different mechanisms for securing or locking with a complementary hole, slot, tab, and/or extrude. In an example, each adjustment mechanism 130 and 140 can be any one of the knob type 'A', 'B', and 'C' to lock and be secured with a respective hole or slot. In an example, the respective hole can be unthreaded, threaded, or partially threaded. In some examples, the various types of adjustment mechanisms shown in FIG. 1D can also be used as securing mechanisms 440 (FIGS. 4A-4B) that are used to secure the base 110 of the cradle assembly 100 to the platform 104.

In some implementations, the type of adjustment mechanisms 130, 140 that are used may be based on amounts of torque applied by the adjustment mechanisms 130, 140 or tolerances in unexpected movements in the components of the cradle assembly 100, which may be based on a type of procedure being performed on the patient whose head is connected to the cradle assembly 100 or a condition of the patient. For example, adjustment mechanisms 130, 140 that include screws with threads (e.g., knobs A and D) may be used in implementations having low tolerances for unexpected movement of the cradle assembly 100 that may require higher amounts of torque applied by the adjustment mechanisms 130, 140. In addition, any of the features of any of the types of knobs shown in FIG. 1D can be combined with any of the features shown in any other type of knob. In some examples, the knobs shown in FIG. 1D that are implemented as adjustment mechanisms 130, 140 may used for a combination of securing the cradle 120 within the base 110, securing the head fixation ring 106 within the cradle 120, and/or adjusting an angular orientation of the cradle 120 and/or head fixation ring 106.

In a first example, a knob type A can have a threaded screw connected to a thumb knob for turning. The thumb knob can have one or more gripping features to apply a torque. Here a gripping feature is shown to help rotate the thumb knob. In an example the screw can be configured to complement a threading on a respective hole or securing location, such as position slots 222 or 224 in tabs 220 or securing locations 211 (FIGS. 2A-2F) of the base 110, or hole 320 (FIGS. 3A-3B) of the cradle 120. In an aspect, the screw of knob A may have one or more locking threads that are configured to secure knob A within the respective hole, slot, or securing location. In another example, the screw can have machine style thread and a respective nut on an opposite side of a respective hole, slot, or securing location.

In a second example, a knob type B can have a pin and a spring connected to the thumb knob. In some implementations, the spring can be configured to assist with inserting or withdrawing the pin from its respective hole or slot in response to pressure applied to the knob B. In one example, prior to insertion into the respective hole or slot, the spring may be held in a coiled position within a recess of the thumb knob. When the knob B is inserted into the respective hole or slot and pressure is applied to the top of the thumb knob, the spring may be released from the recess in the thumb knob and expand to assist with inserting the pin into the respective hole or slot. In another example, prior to insertion into the respective hole or slot, the spring may be in an expanded, uncoiled position. When knob B is inserted into the respective hole or slot and pressure is applied to the top of the thumb knob, the spring may be compressed into a coiled position so that when knob B is removed from the respective slot or recess by pulling on the thumb knob, the spring uncoils to assist with removing knob B from the respective hole or slot. In an example, the spring can be used for helping with aligning the pin and the respective hole or slot. Here a gripping feature is shown having a lip to help pull the thumb knob against the spring. Here the respective hole or slot can be unthreaded to receive the pin.

In a third example, a knob type C can have a combination of the pin, the spring, the screw and a lever arm connected to the thumb knob. In some examples, the pin, spring, and screw operate as described above with respect to knob types A and B. Here the thumb knob includes the lever arm as a gripping feature for applying additional torque to the knob. In an aspect, the thumb knob can include an adjustable lever that has a clamping component that provides a ratcheting feature which is may be used to secure knob C within the respective hole or slot in implementations where the cradle assembly 100 is in a tight space with low clearance areas surrounding the cradle assembly 100, such as in a MRI chamber. In some examples, the respective hole or slot into which knob C is inserted, such as position slots 222 or 224 in tabs 220 or securing locations 211 (FIGS. 2A-2F) of the base 110, or hole 320 (FIGS. 3A-3B) of the cradle 120 may have a partially unthreaded portion and a partially threaded portion that complements the partially unthreaded portion and the partially threaded portion of the pin and screw.

In a fourth example, a knob type D can have a gear or set of cogs in combination of each of the other types of knobs, where the gear allows for a precise spatial and/or rotational adjustment with a complementary hole, slot, tab, and/or extrude. In some implementations, an amount of spacing between the cogs may be based on a minimum increment of angular adjustment of the cradle 120 that is connected to the base 110 by knob type D adjustment mechanisms 130. For example, based on a determined pitch angle for the patient's head in the cradle assembly, the amount rotation of the knob D can be adjusted by a number of cog rotations that corresponds to a predetermined amount of rotation of the cradle 120 within the cradle assembly 100 in either direction. In addition, the respective hole or slot into which knob D is inserted, such as position slots 222 or 224 in tabs 220 or securing locations 211 (FIGS. 2A-2F) of the base 110, or hole 320 (FIGS. 3A-3B) of the cradle 120 may have complementary grooves or cogs that are configured to receive knob D.

In a fifth example, a knob type E can have an actuator in combination of each of the other types of knobs, where the actuator allows for remote controlling of a position of the adjustment mechanism. For example, actuator may be communicatively coupled to the controller 820 (FIG. 8) that is remote from the cradle assembly 100 through a combination of wired and wireless communication networks as discussed above. In some implementations, the actuator may be a rotary actuator that causes rotational adjustment of the knob, such as when the knob is tightened or loosened within a complementary groove, slot, or hole. In some implementations, when knob E is used as the adjustment mechanism 130 connecting the cradle 120 to the base 110, the rotary actuator may be configured to rotate the knob E by an amount that corresponds to a pitch angle of the patient's head when connected to the head fixation ring 106 that is inserted into the cradle 120. The rotary actuator may be a stepper motor or servomotor to rotate the knob at a controlled speed or by an angular amount.

In some implementations, the rotary actuator may also be included as a part of any of the other types of knobs A-D described above. For example, the rotary actuator may be included as part of knob type D that has a gear with a set of cogs that allows for precise rotational adjustment of the knob. In some implementations, the rotary actuator may be configured to rotate the knob D by a predetermined number of cogs in either direction to achieve a predetermined orientation angle of the cradle 102 and/or head fixation ring 106 within the cradle assembly 100. In some implementations where the orientation angle of the cradle 120 can be remotely adjusted by a controller 820 of a computing system, the controller 820 may output a control signal to the actuator to rotate the knob by a predetermined number of cogs, which corresponds to a specific amount of angular orientation adjustment.

In other examples, instead of or in addition to the rotary actuator, the knob type E may include a linear actuator that may be configured to extend or withdraw the knob within the complementary groove, slot, or hole. In some implementations, the linear actuator may be a hydraulic actuator, pneumatic actuator, servomotor or closed-loop stepper motor actuator. In some implementations, pneumatic actuators may be used in examples where there is a pneumatic air source nearby, such as in an operating room or hospital room. Servomotor actuators may be used in examples that may necessitate a high degree of precision and/or accuracy of movement. In some implementations, the linear actuator may also be included as a part of any of the other types of knobs A-D described above. For example, if the linear actuator is included as a part of knob types B or C, the linear actuator may be used to either resist or assist motion of the spring when inserting or withdrawing the knob from the respective hole or slot.

Figure 2B:
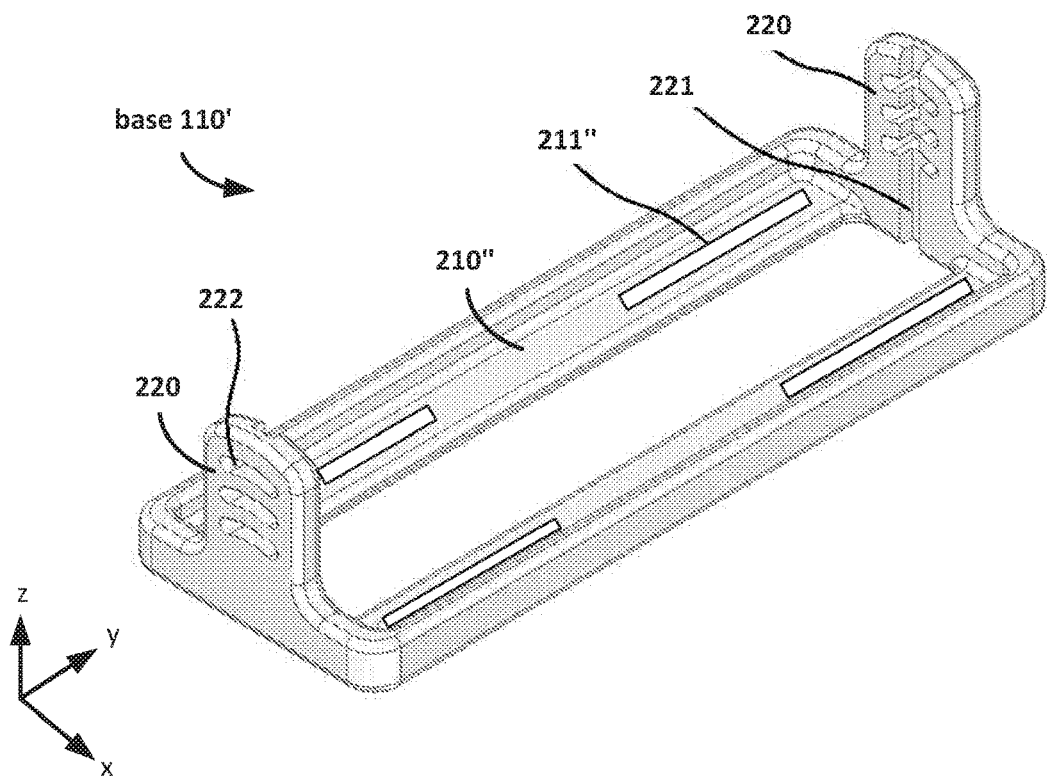

Turning to FIGS. 2A-2B, perspective views of base 110' for cradle assembly 100 are illustrated. For example, FIG. 2A shows a perspective view of the base 110' including a frame 210' having an upper face and a lower face that are in an x-y plane, and a left end and a right end about a plane in a y-direction. At a midpoint in the y-direction, the base 110' can be symmetrical about the x-y plane. In some implementations, the symmetrical design of the base 110' may negate an opportunity for a backwards installation of the base 110' on the platform 102. Each end of the frame 210' may have a tab 220 extruding from an upper surface. In some examples, each tab 220 can have a pin slot 221 and one or more position slots 222 configured to receive the securing mechanisms 130 that connect the cradle 120 to the base 110'. In some aspects, each pin slot 221 may be a vertical opening on an inside face of the tab 220 which extends a full height of the tab 220. In other examples, the pin slot 221 may extend only a portion of the height of the tab 220, such as along a height of the tab 220 that intersects the one or more position slots 222.

In some implementations, the frame 210' may have one or more securing locations 211' passing through the upper surface and the lower surface configured to receive securing mechanisms 440 (FIGS. 4A-4B) that are configured to secure the base 110 to the platform 102. In some examples, the securing location 211' may be a set of holes can be arranged along a y-direction in between the tabs 220 around a periphery of the frame 210'. In some examples, the frame 210' may include multiple sets of holes disposed around the periphery of the frame 210'. For example, the frame 210' may include four sets of holes such that two sets of holes are disposed on each side of the frame 210' and on either side of each of the tabs 220. In other examples, the holes of the securing location 211' may also include greater or fewer sets of holes than those shown in FIG. 2A. In an example, each hole may not include threads and be a smooth pass through to a threaded hole on the platform 102 or the head coil support 104. In another example, each hole can be threaded that are configured to receive a securing mechanism having a threaded screw. Each hole is shown having a circular shape but alternatively can have other shapes such as a teardrop shape, as well as a raised portion and a dent to help with alignment and fixation.

In an example, each position slot 222 can have a series of grooves or cogs (not shown) that correspond with a set of incremental angular adjustments of the cradle 120 that is connected to the base 110' at the position slots 222 by adjustment mechanisms 130. Each groove or cog can correspond to a precision amount of the angle adjustment. In some implementations, the grooves or cogs of the precision cogs may be configured to receive the type D knobs that may have complementary gear teeth or cogs. In addition, the knob D may include a rotary actuator that provides for remotely causing rotation of the knob D within the position slot 222 by a predetermined amount corresponding to a predetermined angular orientation of the cradle 120. In an example, each position slot 222 can have a fiducial mark (not shown) corresponding with each incremental angular adjustment or each positional setting.

FIG. 2B shows a perspective view of the base 110' according to another example. In some implementations, the base 110' may include a frame 210" having a set of securing locations 211". Each securing location 211" can be a slot or opening through an upper face and a lower face of the frame 210". The slot of each securing location 211" can have a shape which allows a pin or a screw to pass through but not a knob of the securing mechanism 440 such that the knob of the securing mechanism 440 is adjacent to an upper surface of the base 110' when inserted through the securing location 211". In some examples, the frame 210" may include multiple sets of slots disposed around the periphery of the frame 210". For example, the frame 210" may include four sets of slots such that two sets of slots are disposed on each side of the frame 210" and on either side of each of the tabs 220. In other examples, the holes of the securing location 211" may also include greater or fewer sets of holes than those shown in FIG. 2B.

Figure 2D:
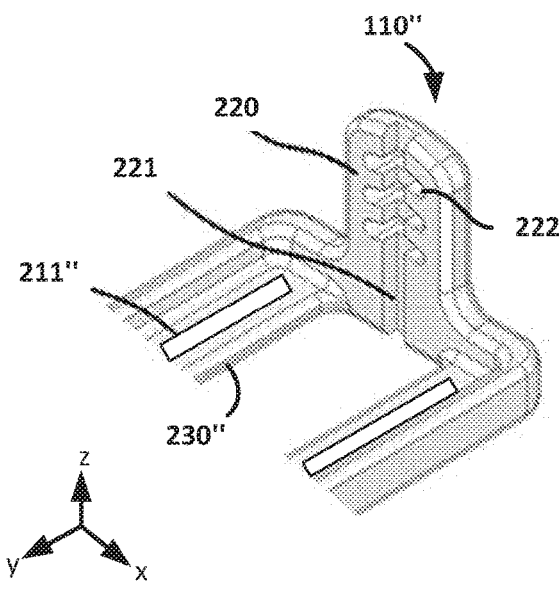
Figure 3B:
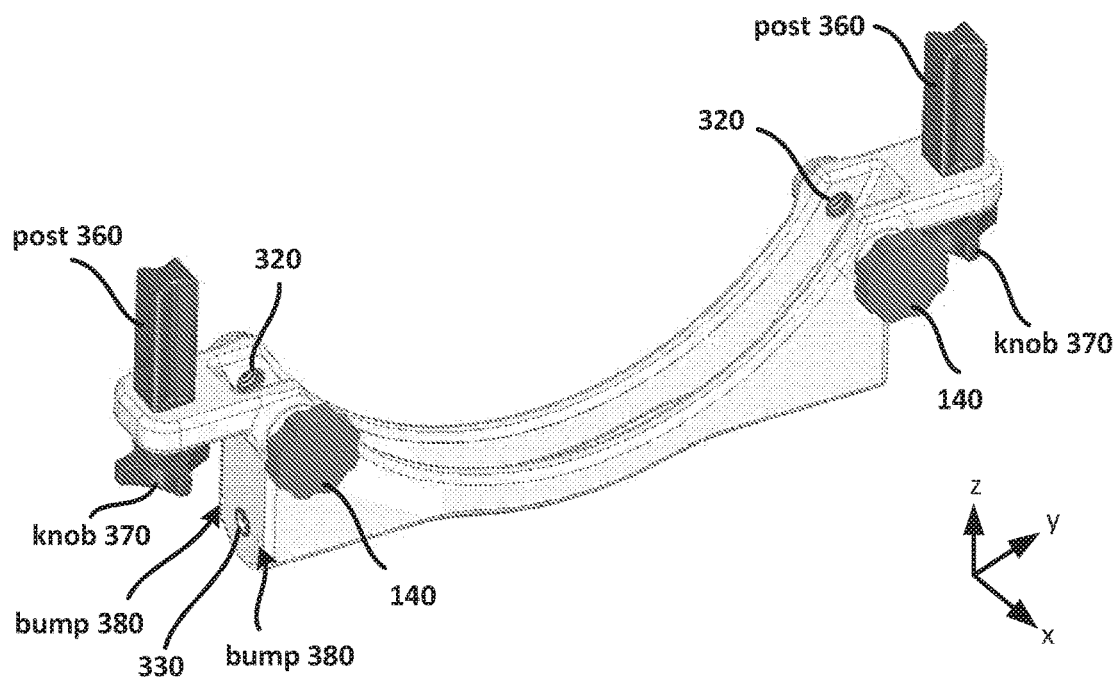
FIG. 3B illustrates another perspective view of the cradle including a pair of posts and the knobs that are configured to lock the head fixation ring in a channel of the cradle.

Turning to FIGS. 2C-2D, implementations of the base 110 for the cradle assembly 100 are illustrated. For example, FIG. 2C shows a perspective view of a bracket section of a two-piece base 110". In some implementations, the base 110" may include a frame 230' having an upper face and a lower face that are in an x-y plane, and a left end and a right end about a plane in a y-direction. The left end of the frame 230' has the tab 220 extruding from the upper face. In one example, the tab 220 may have a pin slot 221 and one or more position slots 222. Each pin slot 221 can be a vertical opening on an inside face of the tab 220 which extends a full height or a partial height of the tab 220. Each position slot 222 can be a horizontal opening that perforates each tab 220 and extends to a partial or full width of the tab 220. In some implementations, the horizontal opening of each position slot 222 can have a curved shape. In an example, the curved shape of the horizontal opening of each position slot 222 can be configured to compensate for a vertical displacement of the patient's head relative to the platform 102 during the pitch adjustment. In other examples, each position slot 222 may have a substantially straight shape such that the position slot 222 extends horizontally across the width of the tab 220 or vertically across the length of the tab 220.

In some implementations, each position slot 222 disposed on the tabs 230 of the base 110 can be arranged on the tab 220 at a predetermined vertical interval. In some examples, the tabs 230 may include position slots that are equally spaced or unequally spaced in a vertical direction along the z-axis. As discussed above, the frame 230' may have a securing location 211' (also referred to as holes 211') such as a set of holes through the upper surface and the lower surface. The securing location 211' can be arranged along a y-direction from the tab 220 toward the right end of the frame 230'.

FIG. 2D shows a perspective view of a partial base 110" according to another example. The base 110" is similar to the base 110', where the base 110" includes a frame 230" having a set of securing locations 211". Each securing location 211" (also referred to as slot 211") can be a slot or opening through an upper face and a lower face of the frame 230". The slot of each securing location 211" can have a shape which allows a pin or a screw to pass through but not a knob of the securing mechanism 440. In some implementations, the slot 211" provides the ability to adjust a position of the securing mechanism 440 connecting the cradle assembly 100 to the platform 104 by sliding the securing mechanism 440 within the slot 211" without having to completely remove the securing mechanism 440 from securing location, such as the hole 211' (FIG. 2A) and subsequently reinsert the securing mechanism 440 into another hole 211'.

In some implementations, the slot 211" may provide for remote adjustment of the securing mechanism 440 within the slot 211". For example, the securing mechanism 440 may include an actuator (e.g., knob E shown in FIG. 1D) that is configured to cause translation of securing mechanism 440 within the slot in response to an actuation signal received from a controller 820 (FIG. 8), which may be remote from the cradle assembly 100. In some implementations, the actuator for the securing mechanism 440 may include linear actuators that allow for remote operation such as hydraulic actuators, pneumatic actuators, spring actuators, servomotor or closed-loop stepper motor actuators. In some implementations, pneumatic actuators may be used in examples where there is a pneumatic air source nearby, such as in an operating room or hospital room. Servomotor actuators may be used in examples that may necessitate a high degree of precision and/or accuracy of movement. In some examples, the actuator for the securing mechanism 440 may be disposed proximate to the slot 211" such that the actuator engages the securing mechanism 440 when inserted into the slot 211".

Figure 2E:
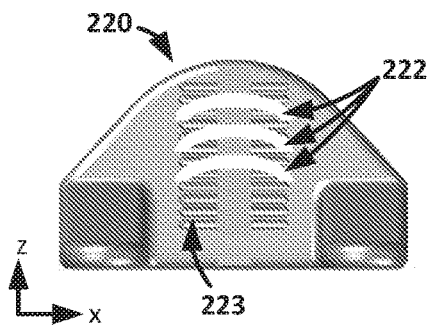
FIG. 2E illustrates a side view of a tab for a base of a cradle assembly.
Figure 2F:
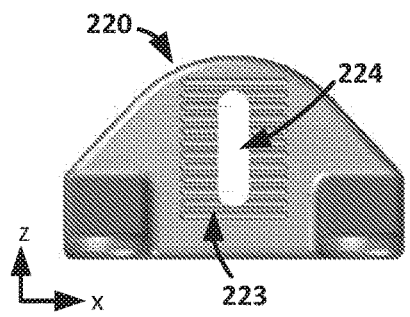
FIG. 2F illustrates a side view of the tab for a base of a cradle assembly.

FIGS. 2E-2F illustrate exemplary side views of a tab 220 for the base 110 of the cradle assembly 100. For example, FIG. 2E shows a side view of a tab 220 including a position slot 222, which may be a horizontal opening that perforates the tab 220 and extends across a partial width of the tab 220. In some implementations, the horizontal opening of the position slot 222 can have a curved shape. In addition, multiple position slots 222 can be arranged on the tab 220 at predetermined vertical intervals. In some examples, the tabs 230 may include position slots 222 that are equally spaced or unequally spaced in a vertical direction along the z-axis. The tab 220 can include a series of grooves 223 to prevent movement while locked to the cradle 120. In one example the series of grooves 223 can be configured to lock the cradle 120 in the set of incremental angle adjustments.

FIG. 2F is a side view of a tab 220 according to another example where a position slot 224 can be a vertical opening that perforates the tab 220 and extends to a partial height of the tab 220 according to an example. The tab 220 can include the series of grooves 223 to prevent movement while locked to the cradle 120. In one example the series of grooves 223 can be configured to lock the cradle 120 in a set of incremental angle adjustments that correspond to predetermined pitch angles of the patient's head when connected to the cradle assembly 100.

Figure 2G:
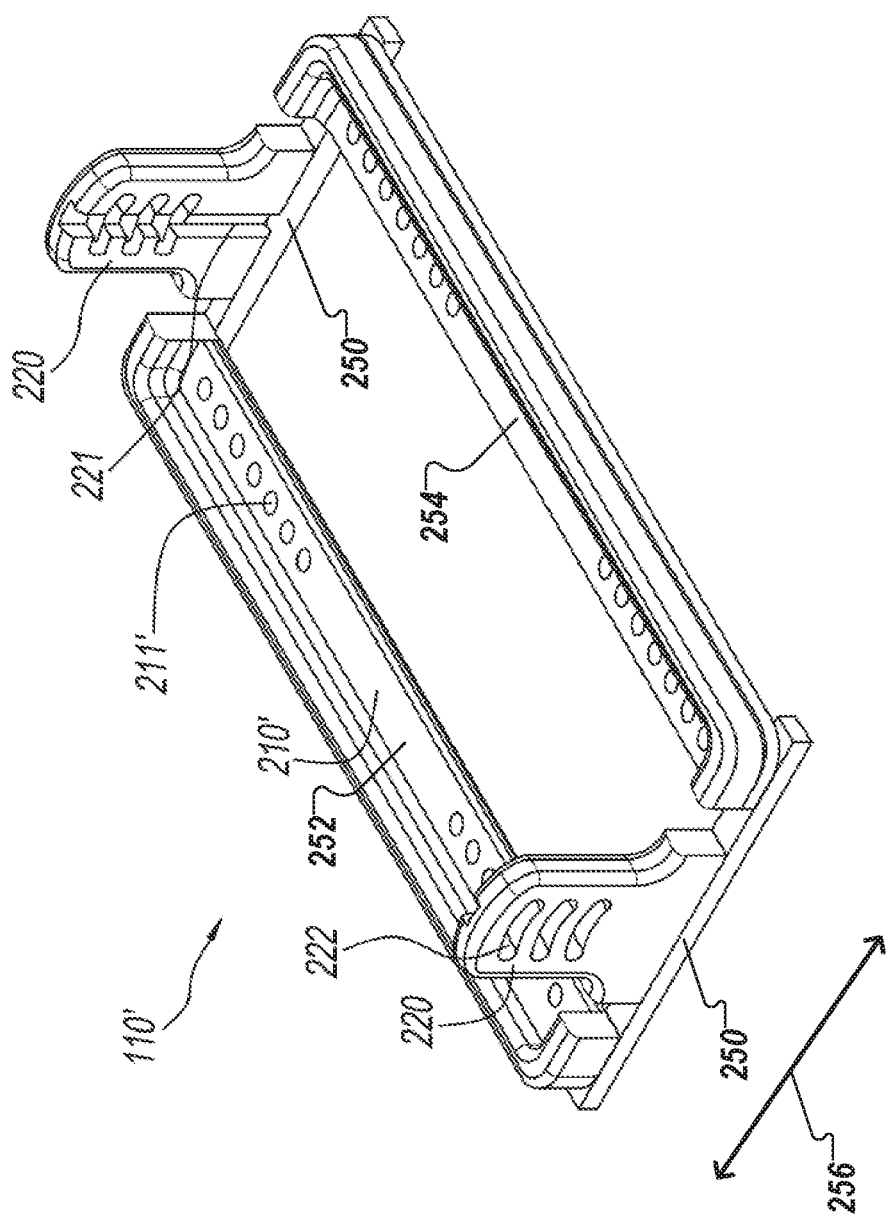
FIGS. 2G and 2H illustrate a perspective view of an extendable base.
Figure 2H:
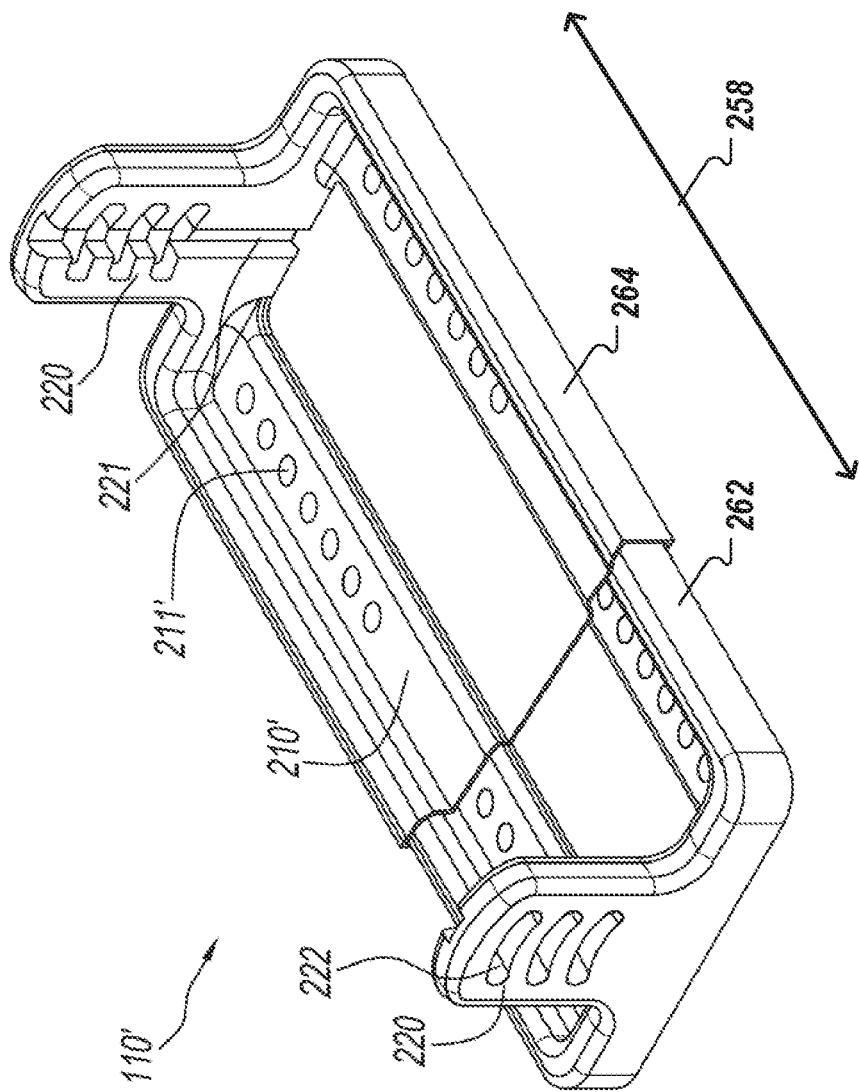

Turning to FIGS. 2G-2H, implementations of a base 110' with a frame 210' having an adjustable length or width are illustrated. In some examples, the dimensions of the base 110' may be adjusted based on variations in dimensional characteristics of the platform 102, head coil support 104, cradle 120, or head fixation ring 106. For example, as shown in FIG. 2G, the frame 210' of the base 110' may include extension bars 250 on each side of the frame 210' that are connected a lower surface beneath the tabs 220 that allow the length (e.g., in direction shown by arrow 256) of the frame 210 to be adjusted on either side of the tabs 210. In some implementations, an upper surface of the extension bars 250 may include a groove or guide rail that provides a translation path for a first frame member 252 and a second frame member 254 to translate across the upper surface of the extension bars 250. In addition, the first and second frame members 252, 254 may be secured to the extension bars 250 by fasteners (not shown) when the frame 210' is at a desired length.

In addition, FIG. 2H shows an example of a base 110' having an adjustable width that can be modified (e.g., in direction shown by arrow 258) based on variations in dimensional characteristics of the platform 102, head coil support 104, cradle 120, or head fixation ring 106. For example, the width of the base 110' may be extended to accommodate a cradle 120 having an extended width for a wider head fixation ring 106 configured for a patient with a larger head size. In some implementations, the frame 210' of the base 110' shown in FIG. 2H may include a first frame portion 262 that is configured to translate along an inner surface of a second frame portion 264 to adjust the width of the frame 210'. In some examples, the first frame portion 262 has a dimensions that correspond to the dimensions of the second frame portion 264 that provide for smoothly translating the first frame portion 262 within a hollowed out region of the second frame portion 264. In addition, the first frame portion 262 may be secured to the second frame portion 264 by one or more fasteners (not shown) when the frame 210' is at a desired width.

Figure 3C:
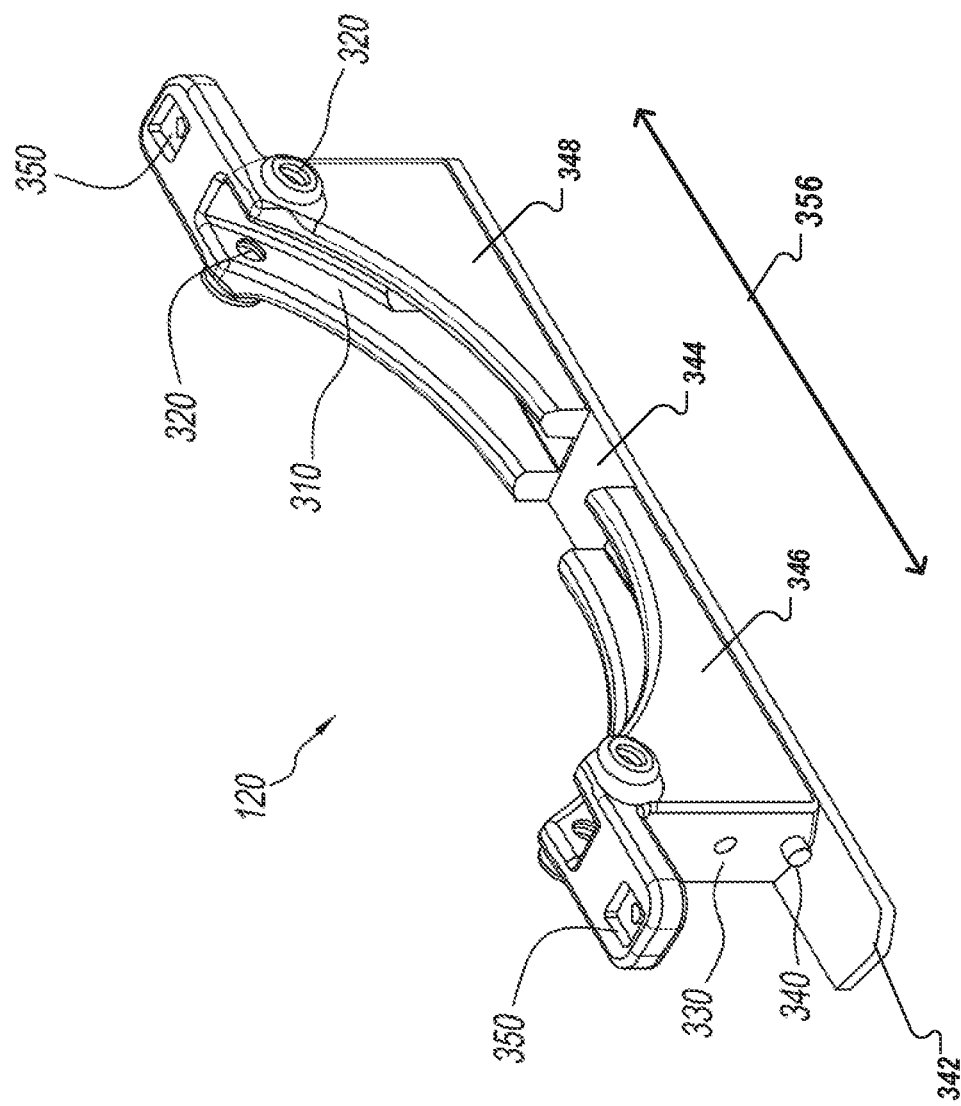
FIG. 3C illustrates a perspective view of an extendable cradle.

Turning to FIGS. 3A-3C, exemplary views of a cradle 120 for the cradle assembly 100 are illustrated. FIG. 3A shows a perspective view of the cradle 120 including a pair of extrudes 340 according to an example. In addition, FIG. 3B shows another perspective view of the cradle 120 including a pair of posts 360 and adjustment mechanisms 140 that are configured to lock the head fixation ring 106 into a channel 310 of the cradle 120 according to another example.

In some implementations, the cradle 120 may be symmetrical about a plane parallel to a left face and a right face of the cradle 120 in the y-direction and about a plane parallel to a front face and a back face of the cradle 120 in the x-direction. In some implementations, the symmetrical design of the cradle 120 may negate an opportunity for a backwards installation of the cradle 120 to the platform base 110 of the cradle assembly 100.

According to one example, the cradle 120 may have a width that is substantially equal to or slightly less than a distance between the tabs 220 on the base 110 such that the cradle 120 can be inserted between the tabs 220 of the base while still being able to rotate smoothly about an axis created by a connection between the base 110 and the cradle 120 without the tabs 220 impeding rotational movement of the cradle 120. In some implementations, a top face of the cradle 120 in a z-direction has a channel 310, extending from the left face to the right face of the cradle 120, which accepts the head fixation device 106. In some implementations, a width of the channel 310 corresponds to a width of the head fixation device 106 such that the head fixation device 106 is configured to fit snuggly within the channel 310 without any unexpected movement (e.g., shaking, rocking) of the head fixation device 106 when inserted into the channel 310.

In some implementations, a pair of extrudes 340 may extend orthogonally from the left face and the right face of the cradle 120 that are configured to fit into the pin slot 221 of the base 110 to provide for maintaining alignment of the cradle 120 within the position slots 222 of the tabs 220 when the cradle 120 is connected to the base 110 by adjusting mechanisms 130. In some examples, each extrude 340 can have a cylindrical shape that may allow rotation within each pin slot 221 of the base 110 as the cradle 120 is rotated through a range of orientation angles associated with a pitch angle of the patient's head when connected to the cradle assembly 120. In some aspects, the extrudes 340 may be configured to retract into the left face and right face of the cradle 120, which may occur when pressure is applied to an outer surface of the extrudes 340, causing the extrudes 340 to be pushed into the left and right faces of the cradle 120. In some examples, the retraction of the extrudes 340 may occur in instances where outer surface of an extrude 340 makes contact with another surface, such as an inner surface of the tabs 220 of the base 110.

In some implementations, the cradle 120 may include a pair of holes 330 on the left face and the right face of the cradle 120 through which the adjustment mechanisms 130 are inserted when connecting the cradle 120 to the base 110 of the cradle assembly 100. In an example, each hole 330 can be configured based on the type of securing mechanism 130 that is inserted into the holes 330. For example, at least a portion of an inner surface of each hole 330 may be threaded or have threaded inserts to accommodate threaded adjustment mechanisms 130, such as knob types A and D (FIG. 1D). In another example, the holes 330 may include complementary grooves or cogs that are configured to receive knob type D to provide for adjusting the orientation angle of the cradle 120 by an amount corresponding to a number of cog rotations.

In some examples, each hole 330 can be positioned on the left and right faces of the cradle 120 such that the holes 330 are configured to align with the position slot 222 on the tab 220 when the cradle 120 is connected to the base 110. In some implementations, a pair of securing mechanisms, such as knob types A-E (FIG. 1D) may pass from the outer face of each tab 220 and screw into the holes 330, coupling the cradle 120 to the base 110 or locking the cradle 120 and the base 110" together. In some examples, the vertical position of the cradle 120 can be changed by aligning the holes 330 of the left and right faces of the cradle 120 with an alternate set of position slots 222 on the tabs 220 of the base 110.

In some implementations, the pair of holes 330 into which the adjustment mechanisms 130 are inserted are positioned directly above each extrude 340 on the left face and the right face of the cradle 120. In some examples, the left face and the right face of the cradle 120 may also include one or more bumps 380 that may be configured to prevent inadvertent movement of the cradle 120 while connected to the base 110 according to an example. The one or more bumps 380 can be configured to complement the series of grooves 223 on each tab 220. In some aspects, the bumps 380 may be configured to retract into the right and left surface of the cradle 120 similarly to the retraction of the extrudes 340.

In certain embodiments, the cradle 120 may also include a set of holes 320 disposed on front and back surfaces of the cradle 120 that pass through the channel 310 substantially orthogonally to the front surface and the back surface of the cradle 120 through which the adjustment mechanisms 140 are inserted when securing the head fixation ring 106 within the channel 310 of the cradle 120. In an example, an inner surface of each hole 320 can be configured based on the type of securing mechanism 140 that is inserted into the holes 320. For example, at least a portion of an inner surface of each hole 320 may be threaded or have threaded inserts to accommodate threaded adjustment mechanisms 140, such as knob types A and D (FIG. 1D). In another example, the holes 320 may include complementary grooves or cogs that are configured to receive knob type D to provide for adjusting a roll angle of the head fixation ring 106 within the cradle 120 by an amount corresponding to a number of cog rotations. In some implementations, the set of securing mechanisms 140 are configured to screw into the set of holes 320 and lock the head fixation ring 106 in the channel 310 of the cradle 120. The roll angle of the patient's head in the cradle assembly 100 can be adjusted by rotating the head fixation ring 106 within the channel 310 of the cradle 120.

In some implementations, the cradle 120 can include one or more mounting locations 350 and one or more posts 360 that may be used for mounting various types of equipment to the cradle assembly 100. In one example, the cradle 120 can have a pair of mounting locations 350 adjacent to the left and right faces of the cradle 120 that are configured to receive a pair of posts 360 that extend from an upper surface of the cradle 120 and are connected to the cradle 120 by fasteners such as knob 370. For example, the mounting locations 350 may be disposed on upper surfaces of the cradle 120 that extend horizontally outward from the channel 310 and may be positioned above the left and right faces of the cradle 120.

In some implementations, each mounting location 350 can be a recessed cutout of the cradle 120 that is sized to fit a post 360 with a minimal clearance, as well as have a hole within the recessed cutout that passes through the upper surface cradle 120 and is configured to receive a knob 370 for securing the post 360 to the cradle 120. For example, each post 360 may also have a complementary hole disposed on a bottom surface of the post 360 that can be configured to secure the post 360 to the mounting location 350 by a knob 370 inserted from the bottom face of the cradle 120 and into the post 360. In some examples, the knob 370 may be any type of fastener such as the knobs A-E described above (FIG. 1D).

In some implementations, each mounting location 350 on the cradle 120 can be configured to have a shape that is complementary to a shape of a bottom surface of the cradle in order to securely align the post 360 within the mounting location 350. For example, the mounting location 350 may have a square, rectangular, circular, or oval shape. In an example, the recessed cutout of the cradle 120 forming the mounting location 350 can have a square shape such that when installing the post 360, the post 360 can be installed at any orientation with 90° intervals. In an example, a post 360 may have a set of angled grooves machined into one or more side surfaces of the post 360 to give the post 360 a "dovetail" cross section that provides better mating with certain types of Image Guidance System (IGS) clamps that may be mounted to the posts 360. In one example, the post 360 can be made of a material having high strength and relatively low ductility, such as a brass material.

In some examples, each post 360 can be configured to provide a rigid mounting location for an IGS reference array clamp. The posts 360 can be utilized in a trajectory planning stage to mount a reference array, such as a reference guide of an image-guided surgery system. In particular, a tracking instrument may be attached to the posts 360 to locate the head fixation ring 106 (and therefore the other components of the surgery system, including a head coil etc.) in a rendered space. A reference array utilized in image-guided surgery can be utilized with the posts 360. In an example, each post 360 can include a sensor configured to detect an angle of the cradle 120, and in effect the head fixation ring 106, relative to the base 110, the cradle assembly 100, and the platform 102. In some implementations, the sensor disposed on or within the post 360 can be used instead of or in addition to the sensors described above to determine the angular orientation of the cradle 120 and/or head fixation ring 106 within the cradle assembly 100.

Turning to FIG. 3C, an implementation of a cradle 120 having an adjustable width is illustrated. In some examples, the width of the cradle 120 may be adjusted based on variations in dimensional characteristics of the platform 102, head coil support 104, base 110, or head fixation ring 106. For example, the width of the cradle 120 may be extended to accommodate a wider head fixation ring 106 for a patient with a larger head size. Similarly, the width of the cradle 120 may be reduced to accommodate a narrower head fixation ring 106 for a patient with a smaller head size. In some implementations, the cradle 120 may include an extension bar 342 to which a first cradle portion 346 and a second cradle portion 348 may be mounted. In some examples, the first and second cradle portions 346, 348 may translate across an upper surface of the extension bar 342 to adjust the width of the cradle 120. In one example, an upper surface of the extension bar 342 may include a groove or guide rail that provides a translation path for a first and second cradle portions 346, 348 to translate across the upper surface of the extension bar 342. In some examples, as the width of the cradle 120 is increased, a gap 344 may exist between the first and second cradle portions 346, 348. In addition, the first and second cradle portions 346, 348 may be secured to the extension bar 342 by fasteners (not shown) when the cradle 120 is at a desired width.

Turning to FIGS. 4A-4B, perspective views of the cradle assembly 100 attached to the platform 102, the head coil support 104, and the head fixation ring 106 are illustrated. For example, FIG. 4A illustrates an example of cradle assembly 100' attached to the platform 102, the head coil support 104, and the head fixation ring 106. The set of securing locations 211, as shown in FIGS. 2A-2D, may allow the cradle assembly 100' to be fixed in various lateral positions with a set of securing mechanisms 440. In some examples, the securing mechanisms 440 can be any type of knob A-E described above (FIG. 1D). In some examples, the lateral position of the cradle assembly 100' on the platform 102 can be adjusted by adjusting the positions of the securing mechanisms 440 within the set of securing locations 211' with respect to the platform 102 or the head coil support 104. In one example, a lateral adjustment of the base 110 with the platform 102 or head coil support 104 can include ±25 mm and 0 mm.

FIG. 4B is a perspective drawing of the cradle assembly 100" attached to the platform 102, the head coil support 104, and the head fixation ring 106 according to an example. The set of securing locations 211' on the base 110" allows the cradle assembly 100" to be fixed in a varying lateral position with the set of knobs 440. In some examples, the lateral position of the cradle assembly 100' on the platform 102 can be adjusted by adjusting the positions of the securing mechanisms 440 within the set of securing locations 211' with respect to the platform 102 or the head coil support 104. In one example, a lateral adjustment can include ±25 mm and 0 mm.

In some implementations, the slot 211" (FIGS. 2B and 2D) may provide for remote adjustment of the securing mechanism 440 within the slot 211", which allows for remote lateral adjustments of the base 110" of the cradle assembly 100 on the platform 102 or head coil support 104. For example, the securing mechanism 440 may include an actuator (e.g., knob E shown in FIG. 1D) that is configured to cause translation of securing mechanism 440 within the slot in response to an actuation signal received from a controller 820 (FIG. 8), which in turn causes lateral translation of the base 110" along an upper surface of the platform 102 or head coil support 104. In some implementations, the actuator for the securing mechanism 440 may include linear actuators that allow for remote operation such as hydraulic actuators, pneumatic actuators, spring actuators, servomotor or closed-loop stepper motor actuators. In some implementations, pneumatic actuators may be used in examples where there is a pneumatic air source nearby, such as in an operating room or hospital room. Servomotor actuators may be used in examples that may necessitate a high degree of precision and/or accuracy of movement. In some examples, the actuator for the securing mechanism 440 may be disposed proximate to the slot 211" such that the actuator engages the securing mechanism 440 when inserted into the slot 211".

Turning to FIGS. 5A-5C, a series of drawings in a y-plane demonstrating a pitch adjustment of the cradle assembly 100 creating a pitch angle between the head fixation ring 106 relative to the platform 102 and the head coil support 104 are illustrated. In some implementations, the pitch angle can be adjusted by tightening the adjustment mechanisms 130 at different spots along the position slot 222 of the base 110. This action demonstrates an adjustment mechanism of the cradle assembly 100. In one example the pitch angle can be adjusted to one or more angle adjustments including 0°, ±6.6°, ±13°, ±19.1°, ±24.7°, and ±29.9°.

In one example, each adjustment mechanism 130 may be controlled or adjusted independently of the other adjustment mechanism 130. Alternatively, both adjustment mechanisms 130 can be configured to adjust or rotate simultaneously. In one example, at least one adjustment mechanism 130 can be configured to be the knob type 'D' such that the pitch angle can be adjusted with a gear, while the other adjustment mechanisms 130 is unlocked. In one example, one adjustment mechanism 130 can be configured to control the adjustment, while another adjustment mechanism 130 can have a series of measured resting points within the position slot 222, such that a cog may "click" at a discrete measured position between two measured resting points. In one example, locking of one adjustment mechanism 130 at the discrete measured position may cause locking of the other adjustment mechanism 130.

In an aspect, an adjustment of the pitch angle of the cradle 120 can also result in an adjustment of a longitudinal position of the cradle 120 relative to the platform 102. This adjustment of the longitudinal position of the cradle 120 can be configured to compensate for a longitudinal displacement of the patient's head relative to the platform 102 during the pitch angle adjustment. Similarly, in an aspect, the pitch adjustment can also adjust a vertical position of the cradle 120 relative to the platform 102. This adjustment of the vertical position of the cradle 120 can be configured to compensate for a vertical displacement of the patient's head relative to the platform 102 during the pitch adjustment. In an example, the adjustment mechanism 130 configured for the pitch angle adjustment can simultaneously adjust the longitudinal position and the vertical position of the cradle 120 relative to the platform 102.

In some implementations, in addition to tightening of the adjustment mechanisms 130 within the holes 330 of the cradle 120, rotation of the adjustment mechanisms 130 connecting the base 110 to the cradle 120 may also cause angular rotation of the cradle 120, which may result in adjustment of the pitch angle or orientation angle of the cradle 120 and/or head fixation ring relative to the base 110 and/or platform 102. In some implementations, when the knob type D (FIG. 1D) is used as the adjustment mechanism 130, an amount of spacing between the cogs may be based on a minimum increment of angular adjustment of the cradle 120 that is connected to the base 110 by knob type D adjustment mechanisms 130. For example, based on a determined pitch angle for the patient's head in the cradle assembly, the amount rotation of the knob D can be adjusted by a number of cog rotations that corresponds to a predetermined amount of rotation of the cradle 120 within the cradle assembly 100 in either direction.

In implementations where rotation of the adjustment mechanisms 130 causes angular adjustment of the cradle 120, the adjustment mechanisms 130 may be manipulated manually by a user or remotely by a controller 820 of a computing system in response to manual or automatic actuation by the controller via a wired or wireless communication network. In some implementations, the actuator may be a rotary actuator that causes rotational adjustment of the knob, such as when the knob is tightened or loosened within a complementary groove, slot, or hole. In some implementations, when knob E is used as the adjustment mechanism 130 connecting the cradle 120 to the base 110 or when knob D includes an actuator, the rotary actuator may be configured to rotate the knob E by an amount that corresponds to a pitch angle of the patient's head when connected to the head fixation ring 106 that is inserted into the cradle 120. The rotary actuator may be a stepper motor or servomotor to rotate the knob at a controlled speed or by an angular amount.

In examples where the rotary actuator may be included as part of knob type D that has a gear with a set of cogs that allows for precise rotational adjustment of the knob, the rotary actuator may be configured to rotate the knob D by a predetermined number of cogs in either direction to achieve a predetermined orientation angle of the cradle 102 and/or head fixation ring 106 within the cradle assembly 100. In some implementations where the orientation angle of the cradle 120 can be remotely adjusted by a controller 820 of a computing system, the controller 820 may output a control signal to the actuator to rotate the knob by a predetermined number of cogs, which corresponds to a specific amount of angular orientation adjustment.

In some implementations, the controller 820 may be configured to automatically adjust the pitch angle of the cradle 120 within the cradle assembly 100 based on sensor data received from one or more sensors disposed on or within the components of the cradle assembly 100, such as the base 110, cradle 120, and/or head fixation ring 106. For example, once a trajectory planning procedure is complete, one or more trajectory data points may be input to the computing system via an input/output device, such as a computer workstation, and the controller 820 may output control signals to the actuators associated with the adjustment mechanisms 130 to adjust the pitch angle of the cradle 120. In some examples, the patient's head may or may not be connected to the cradle assembly 100 during the automatic angular adjustment of the cradle 120. In addition, the controller 820 may be configured to control the pitch angle of the cradle through a range of angular adjustments, such as the adjustments shown in FIGS. 5A-5C.

For example, FIG. 5A is a drawing of the cradle assembly 100 creating a first pitch angle 510 between the head fixation ring 106 relative to the platform 102 and the head coil support 104 according to an example. The first pitch angle is shown as an obtuse angle relative to an upper end (e.g., an end of the platform 102 extending away from the head and body of the patient or the end of the platform 102 on which the cradle assembly 100 is configured) of the platform 102 and/or the base 110 in the x-direction.

After a patient is sedated, and a trajectory planning procedure is completed, a mini frame and/or the head fixation ring 106 can be attached to the patient's head. The head fixation ring 106 can be secured to the cradle 120 in, e.g., an operating room in which the trajectory planning procedure is conducted. A patient's head can be fixed to the head fixation ring 106 by a set of fixation pins 520. In some implementations, when the patient's head is seated properly within the cradle 120, the angular orientations of the cradle 120 and head fixation ring 106 relative to the base 110 and/or platform 102 may be substantially equal, and differences in the angular orientations of the cradle 120 and head fixation ring 106 by more than a threshold amount may indicate that the head fixation ring 106 is not seated properly within the cradle 120 and may require reseating.

FIG. 5B is a drawing of the cradle assembly 100 creating a second pitch angle 511 between the head fixation ring 106 relative to the platform 102 and the head coil support 104 according to an example. The second pitch angle is shown as a right angle relative to the platform 102 in the x-direction. Similarly, FIG. 5C is a drawing of the cradle assembly 100 creating a third pitch angle 512 between the head fixation ring 106 relative to the platform 102 and the head coil support 104 according to an example. The third pitch angle is shown as an acute angle relative to the upper end of the platform 102 and/or base 110 and/or base 110 in the x-direction.

Figure 6:
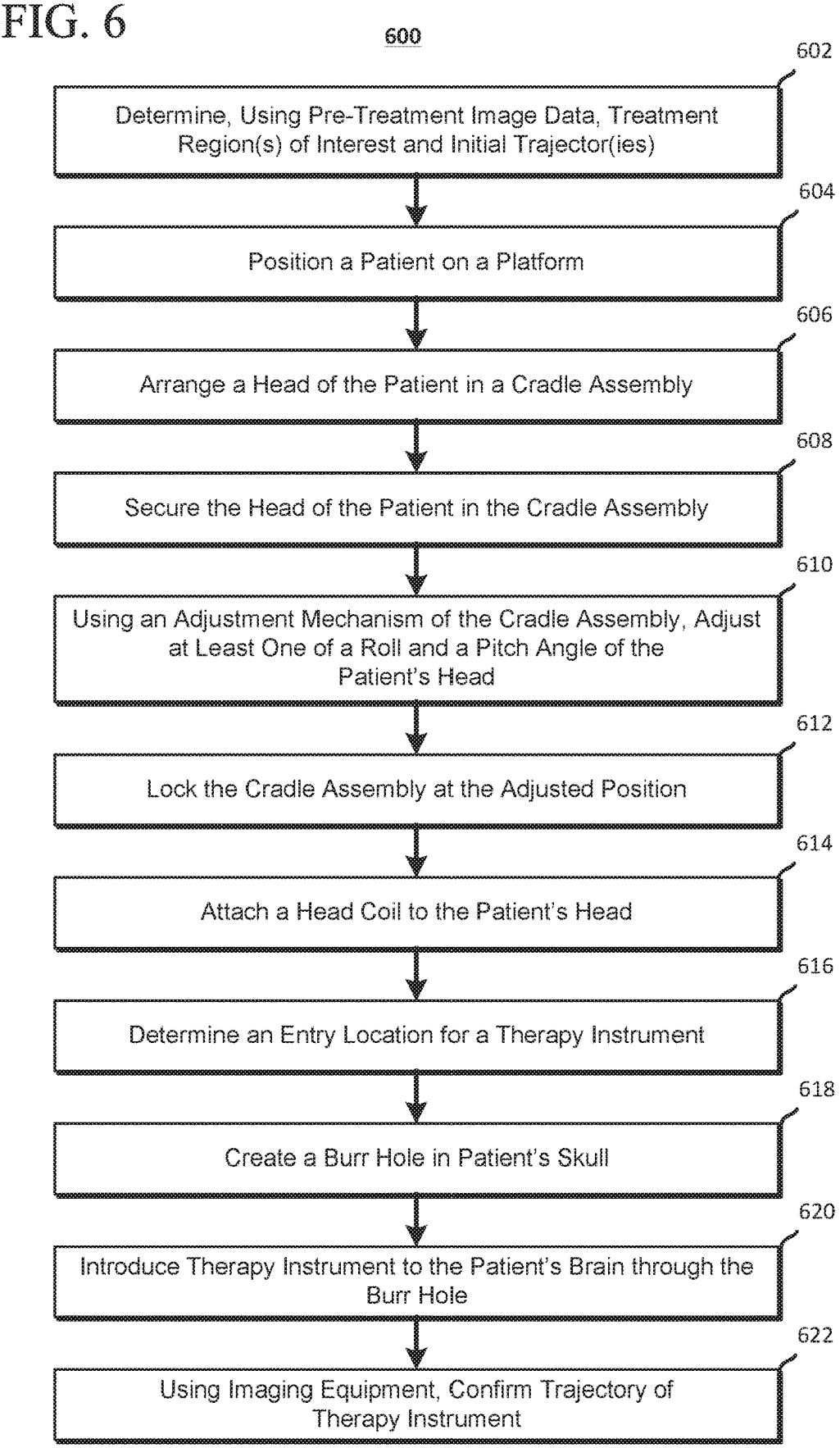
FIG. 6 is a flow chart of an example method for using a cradle assembly.
Figure 7:
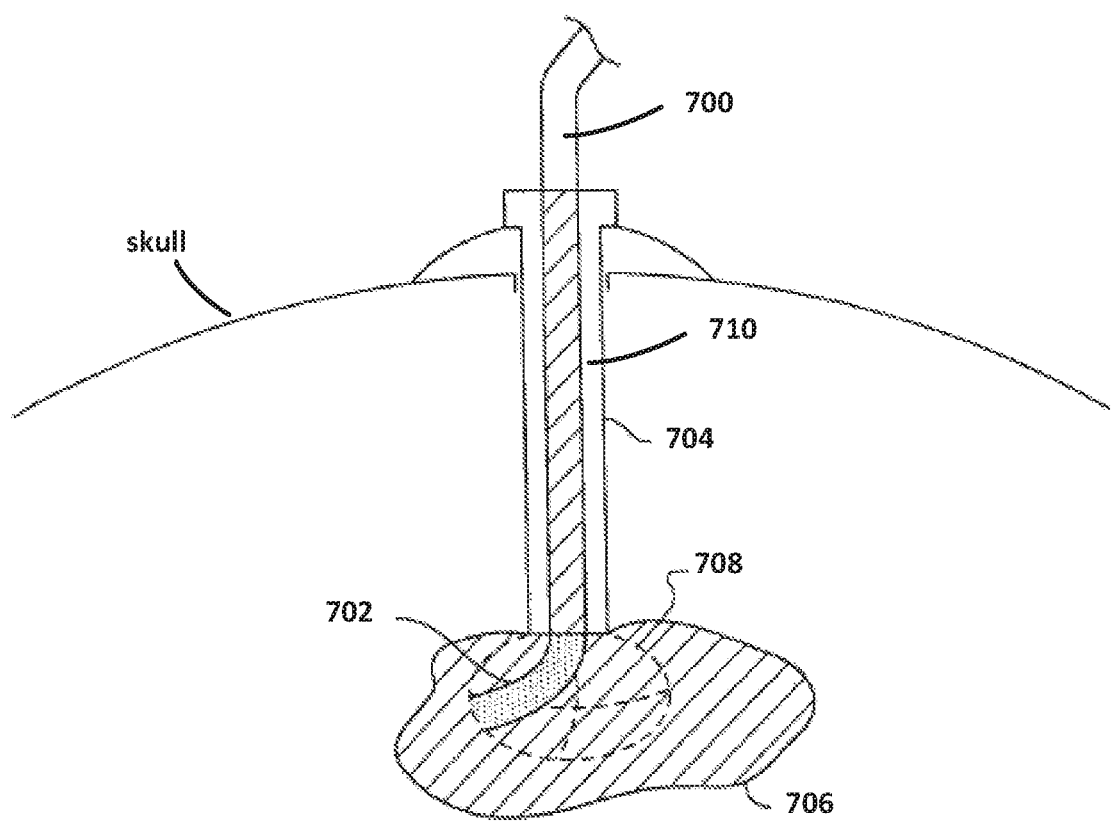
FIG. 7 is an illustration of a cross-section of a patient's skull having a burr hole and a therapy device deployed into a region of interest in the patient's skull.

FIG. 6 illustrates an exemplary flow chart of an example method 600 for using a cradle assembly 100, and FIG. 7 is an accompanying illustration of a cross-section of a patient's skull having a burr hole 710 and a therapy device 700 and/or probe introduction equipment deployed into a region of interest (ROI) 706 in the patient's skull when the patient's head is connected to the cradle assembly 100.

In pre-planning a treatment, in certain embodiments, a pre-treatment image data such as Digital Imaging and Communications in Medicine (DICOM) data can be loaded and co-registered. Using the pre-treatment image data, one or more ROI's 706 and/or targeted tissue areas or volumes and one or more initial trajectories can be determined and set (602). After a treatment volume has been identified, or several volumes have been identified, a trajectory for affecting a treatment to the volume(s) can be planned. A recommended head position setting may be included in trajectory planning, for example, as described in U.S. Pat. No. 9,211,157 entitled "Probe Driver", the contents of which are hereby incorporated by reference in its entirety. In some implementations, the recommended head position setting may include at least one of a pitch angle for the cradle 120, a roll angle of the head fixation ring 106 positioned within the channel 310 of the cradle, and a lateral position of the base 110 on the platform 102 or head coils support 104.

In some implementations, a patient can be positioned on a table, bed or platform such as the platform 102 of FIGS. 1A and 1B (604) and a head of the patient can be immobilized using the head fixation ring 106. In some examples, the head of the patient can be arranged in the cradle assembly 100 (606) by positioning the head fixation ring 106 within the channel 310 of the cradle 120. Using the adjustment mechanisms 140, the head of the patient can be secured in the cradle assembly 100 (608), according to some implementations.

In some examples, using an adjustment mechanism of the cradle assembly 100, such as the adjustment mechanism 130 and 140 shown in FIGS. 1B and 1C, at least one of the pitch angle and the roll of the patient's head can be adjusted respectively, thereby creating an adjusted position (610). In some examples, the adjustment can be performed manually or automatically via a computing system as discussed further below. In certain embodiments, the patient is positioned on the cradle assembly 100 while within imaging equipment such as an MRI cabin, and imaging is performed to obtain the DICOM data and to plan a trajectory associated with the therapy device 700 and/or probe introduction equipment, as shown in FIG. 7. In an example, the DICOM data can be used to prompt the operator for a recommended head position setting. In an example, a measurement provided by the sensors disposed on or within components of the cradle assembly can be used to confirm that the adjusted position of the cradle assembly 100 is in the recommended head position setting.

The recommended head position setting or adjustments may be based on one or more steps in a method for determining trajectory adjustments based upon initial position and orientation of probe introduction equipment upon the skull of a patient, as described in U.S. patent application Ser. No. 14/661,310 entitled "Image-Guided Therapy of a Tissue" and filed Mar. 18, 2015, the contents of which are hereby incorporated by reference in its entirety.

In some examples, using an adjustment mechanism of the cradle assembly 100, such as the adjustment mechanism 130 and 440 shown in FIGS. 4A and 4B, at least one of the pitch angle and the roll of the patient's head can be adjusted respectively, thereby creating an adjusted position (610).

In some implementations, using the one or more adjustment mechanisms 130, the cradle assembly 100 can be locked at a different recommended head position setting or the adjusted position (612) as shown in FIGS. 5A, 5B, and 5C. In preparation for the treatment, in certain embodiments, a head coil and a fixation or stabilization system can be attached to the patient using the set of fixation pins 520 as shown in FIG. 5A (614), for example by positioning the head coil and the stabilization system on the platform 102 or the head coil support 104.

In some examples, prior to applying the therapy to the ROI 706, a probe entry location into a skull of the patient can be identified (616). In certain embodiments, a burr hole 710 is drilled in the skull (618). A rigid sheath 704 can be inserted into the burr hole 710. The burr hole 710 may be drilled prior to attachment of the probe introduction equipment (e.g., a mini frame, anchoring device, guide stem, instrument sheath, etc.). A twist-drill hole, in certain embodiments, can be created following a trajectory alignment of the probe introduction equipment.

A therapy device 700 and/or probe introduction equipment can be introduced into the patient's brain through the burr hole 710 (620). In certain embodiments, the therapy device 700 and/or probe introduction equipment includes an end portion 702 that can be moved in a range 708. In an example the end portion 702 can be passive or pre-shaped. In another example the end portion 702 can be active or change shape. The end portion 702 can be active or change shape based on the sensor measurement according to an example.

In certain embodiments, the therapy device 700 and/or probe introduction equipment is introduced and monitored in real-time. In certain embodiments, the patient is positioned in imaging equipment such as an MRI cabin, and imaging is performed to confirm a trajectory (622) associated with the therapy device 700 and/or probe introduction equipment. For example, an MRI trajectory wand may be inserted into the probe introduction equipment for use in confirming its trajectory. The trajectory of the probe introduction equipment, for example, can be evaluated using MRI imaging prior to inserting a probe into the brain. Volumetric imaging or volumetric visualization may be captured to include the entire head and full extent of the probe introduction equipment.

Along with trajectory confirmation, in some examples, beam fiducial marker detection may also be performed. For example, the captured images may also display a position of a beam fiducial marker located in a portion of the probe introduction equipment. This beam fiducial marker can be detected and identified by the MRI imaging system and method to store an orientation of the physical direction of the probe. The captured images, in implementations where pre-treatment image data is not available, can be used for planning a therapy session.

In certain embodiments, a probe actuation and guidance device (e.g., a follower) and a test tool can be attached to the probe introduction equipment, to provide positional feedback for a self-test function. The self-test function, for example, may be used to confirm that inputs to the probe actuation and guidance device accurately and/or precisely drive the probe actuation and guidance device or the therapy device 700 and/or probe introduction equipment.

Figure 8:
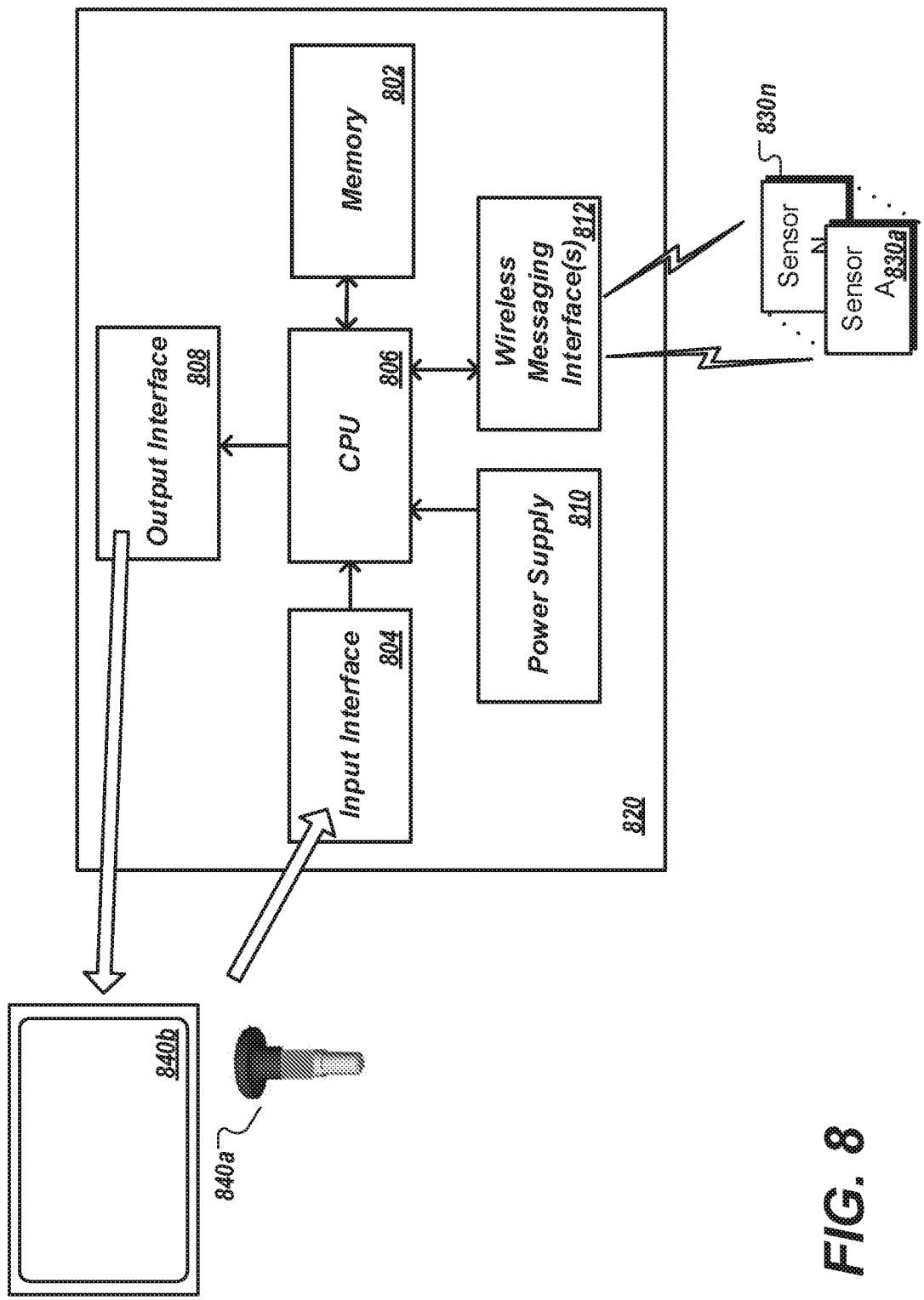
FIG. 8 is a block diagram of example circuitry for controlling remote adjustment of a cradle assembly.
Figure 9:
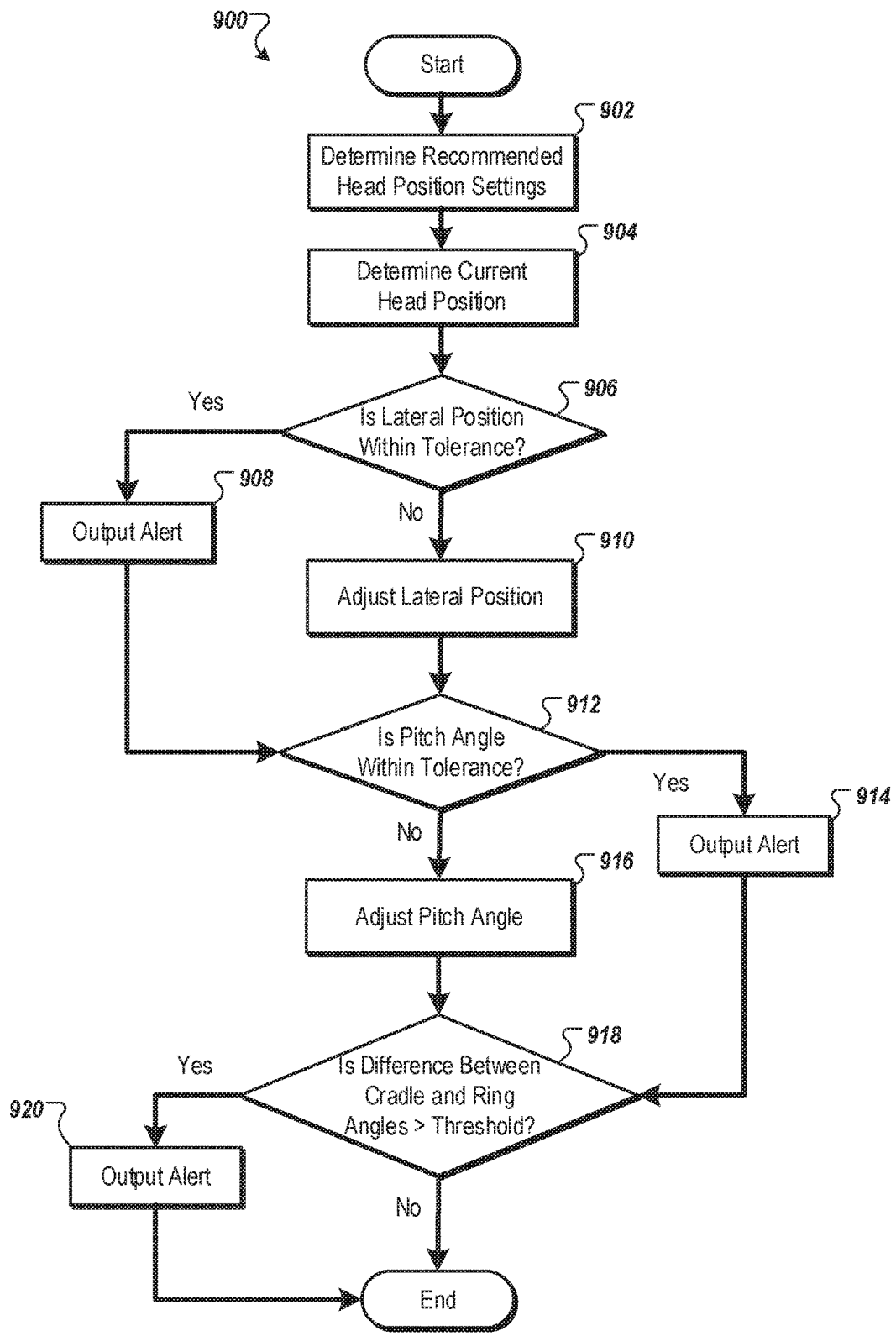
FIG. 9 illustrates an exemplary flow diagram of a method for controlling remote adjustment of a cradle assembly.

In some examples, processing of sensor data obtained by the sensors disposed on or within the components of the cradle assembly 100 and remotely, automatically controlling the pitch angle and position of the cradle assembly 100 may be performed by control circuitry such as a programmable logic controller (PLC) or central processing unit (CPU) that executes one or more software processes and outputs position information to other controllers and/or electronically-activated components. FIG. 8 provides a simplified hardware block diagram of control circuitry 820 of a cradle assembly control system 800. The description of the control circuitry 820 is not meant to be limiting, and can include other components than those described herein. References to control circuitry 820 relate to the circuitry of one or more processing circuits, which can also be referred to interchangeably as processing circuitry. The control circuitry 820 may include a central processing unit (CPU) 806 that executes one or more software processes associated with the system 800. Software instructions for the processes can be stored in memory 802.

In some examples, the memory 802 can include both volatile and non-volatile memory and can store various types of data associated with executing the processes related to collecting sensor data from sensors 830a through 830n, which may include the sensors disposed on or within the components of the cradle assembly 100, such as the base 110, cradle 120, or head fixation ring 106, processing the sensor data to determine a current position, pitch angle, and/or roll angle of the cradle 120 and/or head fixation ring 106, and controlling actuators 840a of the cradle assembly control system 800 to adjust the position and/or pitch angle of the cradle assembly 100.

The control circuitry 820 includes an input interface 804 for communicating with various devices 840 that provide configuration and settings inputs to the control circuitry 820 such as actuators 840a and computer workstation(s) 840b and any other device associated with the system 800. The control circuitry 820 also includes an output interface 808 for connecting and providing information to devices 840 communicating with the control circuitry 820 including the actuators 840a and computer workstation(s) 840b and any other device communicating with the control circuitry 820. The control circuitry 820 also includes a power supply 810, such as a battery connection or wired connection to an electrical power source within the operating room or MRI room. Further, the control circuitry 820 includes one or more communication interfaces 812, which may include wireless messaging interfaces, that enable the control circuitry 820 to collect sensor signals supplied by the sensors 830. In some examples, the sensors 830 may also interface with the system 800 via wired connections to the control circuitry 820.

In some implementations, the memory 802 of the control circuitry 820 includes instructions for executing one or more engines or modules that perform processes associated with collecting and interpreting messages provided by the sensors 830 and communicating information regarding the sensor system to the devices 840. In some implementations, recommended head settings and corresponding configuration parameters for the cradle assembly 100 may be stored in the memory 802.

In some implementations, short range wireless communication is provided through Bluetooth wireless communication technology. In other embodiments, Ultra Wide Band (UWB) or ZigBee wireless communications may be used. The type of wireless communication technology that is used for the implementations described herein can be based on various factors that can include battery life, data usage, security and/or line-of-sight restrictions, and other concerns. In some embodiments, ZigBee or Bluetooth wireless communications may be used in applications where link security is prioritized. In other embodiments where frequency interference is a concern, Bluetooth or UWB communications may be used since both technologies use adaptive frequency hopping to avoid channel collision. In embodiments where a total of frequency channels is prioritized, Bluetooth wireless communications may be used.

While the flow diagram illustrates an ordering of steps or blocks of the method 800, it can be understood that the various steps and processes associated with the method 800 can be performed in any order, in series, or in parallel. In some implementations, the method 800 may be performed instead of or in addition to the manual adjustment of the cradle assembly 100 (610) of the method 600 (FIG. 6). In addition, the method 800 may be performed prior to or subsequent to medical imaging procedures and/or stereotactic radiosurgery.

In some implementations, as described above, a recommended head position setting is determined based on pre-treatment image data such as DICOM data, which can be loaded and co-registered at a computer workstation of the computing system (902). In some examples, using the pre-treatment image data, one or more ROI's 706 and/or targeted tissue areas or volumes and one or more initial trajectories can be determined and set. After a treatment volume has been identified, or several volumes have been identified, a trajectory for affecting a treatment to the volume(s) can be planned. In some implementations, the recommended head position setting may include at least one of a pitch angle for the cradle 120, a roll angle of the head fixation ring 106 positioned within the channel 310 of the cradle 120, and a lateral position of the base 110 on the platform 102 or head coils support 104 and may be based on the one or more initial trajectories for affecting treatment to the target volume(s). The positioning of the cradle 120, in some embodiments, is accomplished at least in part through automated adjustments performed by actuators or gear and linkage systems. For example, a lateral height may be ratcheted up automatically, or a tilt angle may be rotated automatically. In some embodiments, the positioning of the cradle 120 may be accomplished manually. For example, pitch, roll, and/or lateral position settings may be supplied to an operator for manually setting the position of the cradle assembly. The cradle assembly, in some embodiments, may be positioned, at least in part, prior to introducing the head of the patient.

In certain embodiments, once the head of the patient is arranged and secured in the cradle assembly, a current head position may be determined, which may be based on sensor data received from the sensors disposed on or within the components of the cradle assembly 100 including at least one of the base 110, cradle 120, and/or head fixation ring 106 (904). In some examples, the current head position may include at least one of a current pitch angle of the cradle 120, a roll angle of the head fixation ring 106 positioned within the channel 310 of the cradle 120, and a lateral position of the base 110 on the platform 102 or head coil support 104.

In other embodiments, rather than determining a current head position, the current probe apparatus mounting position may be determined. For example, positioning of the head can provide for obtaining greater clearance for movement of the probe apparatus and/or access to probe apparatus upon situating the patient in the MRI. In some circumstances, the positioning of the probe apparatus may be altered from the anticipated positioning due to a miscalculation upon creating the bore hole in the patient's skull, for example. Positioning of the probe equipment, for example, may be determined through MRI analysis (e.g., identifying fiducial markers or a test tool positioning). If the probe equipment is offset by more than a threshold tolerance, the system may recalculate positioning of the cradle assembly to provide for desired probe apparatus accessibility and/or manipulation range.

If, in some examples, a difference between the recommended lateral position of the base 110 and the current lateral position of the base 110, is within an allowed tolerance such that the recommended and current lateral positions are approximately equal (906), then the computing system 900 may output an alert to the computer workstation information a user that the cradle assembly 100 is at the recommended lateral position (908). If, however, in some examples, the difference between the recommended and current lateral positions of the base 110 is outside the allowed tolerance, then the controller 820 may output control signals to the actuators for the securing mechanisms 440 that secure the base 110 to the platform 102 or head coil support 104 to modify the lateral position of the cradle assembly 100 (910).

For example, the securing mechanism 440 may include an actuator that is configured to cause translation of securing mechanism 440 within the slot 211" (FIGS. 2B and 2D) in response to an actuation signal received from a controller 820. In some examples, the actuator for the securing mechanism 440 may be disposed proximate to the slot 211" such that the actuator engages the securing mechanism 440 when inserted into the slot 211". In some implementations, when the base 110' reaches the recommended lateral position, the controller 820 may output an alert to the computer workstation to inform a user that the cradle assembly 100 is at the recommended lateral position.

In other embodiments, the system may output instructions for an operator to manually adjust the lateral positioning. For example, instructions may be provided upon a controller for the probe apparatus or upon the display of a workstation configured to control aspects of the medical procedure.

If, in some implementations, a difference between the recommended pitch angle of the cradle 120 and the current pitch angle of the cradle 120, is within an allowed tolerance such that the recommended and current pitch angles are approximately equal (912), then the computing system 900 may output an alert to the computer workstation to inform a user that the cradle assembly 100 is at the recommended pitch angle (914). If, however, in some examples, the difference between the recommended and current lateral positions of the base 110 is outside the allowed tolerance, then the controller 820 may output control signals to the actuators for the adjustment mechanisms 130 that connect the cradle 120 to the base 110 to adjust the pitch angle of the cradle 120 (916).

In other embodiments, the system may output instructions for an operator to manually adjust the pitch angle positioning. For example, instructions may be provided upon a controller for the probe apparatus or upon the display of a workstation configured to control aspects of the medical procedure.

For example, the actuators for the adjustment mechanisms 130 may be rotary actuators that cause rotational adjustment of the knob, such as when the knob is tightened or loosened within a complementary groove, slot, or hole. In some implementations, when knob E is used as the adjustment mechanism 130 connecting the cradle 120 to the base 110 or when knob D includes an actuator, the rotary actuator may be configured to rotate the knob E by an amount that corresponds to a pitch angle of the patient's head when connected to the head fixation ring 106 that is inserted into the cradle 120. In some implementations, when the cradle 120 reaches the recommended pitch angle, the controller 820 may output an alert to the computer workstation to inform a user that the cradle 120 is at the recommended pitch angle.

If, in some examples, if a difference between a pitch angle of the cradle 120 and the head fixation ring 106 is greater than a threshold amount (918), the controller 820 may output an alert to the computer workstation to inform a user that the head fixation ring 106 may not be properly seated in the channel 310 of the cradle 120 (920). In some implementations, when the patient's head is seated properly within the cradle 120, the angular orientations (pitch angles) of the cradle 120 and head fixation ring 106 relative to the base 110 and/or platform 102 may be substantially equal, and differences in the angular orientations of the cradle 120 and head fixation ring 106 by more than a threshold amount may indicate that the head fixation ring 106 is not seated properly within the cradle 120 and may require reseating.

While certain embodiments have been described, these embodiments have been presented by way of example only, and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. An adjustable cradle assembly for adjusting a head fixation apparatus relative to a patient platform, the adjustable cradle assembly comprising:
   a base comprising:
      a locking mechanism for releasably locking the base to the patient platform, and
      a pair of vertical support members, each vertical support member having at least one position aperture for setting a vertical height relative to the platform;
   a cradle comprising:
      a curved channel configured to releasably receive a head fixation ring, wherein the cradle is configured to span between the vertical support members of the base such that the channel aligns between the vertical support members, and
      at least one adjustment connection point that is configured for alignment with a position aperture of a corresponding vertical support member of the pair of vertical support members; and
   at least one adjustment mechanism that is configured to releasably connect to a respective adjustment connection point of the cradle through a selected position aperture of a respective vertical support member of the pair of vertical support members to lock the cradle to the base at a selected lock position;
   wherein, upon locking at the selected lock position, the cradle is aligned at a selected vertical position above the patient platform and at a selected pitch angle relative to a plane perpendicular to the patient platform.

2. The adjustable cradle assembly of claim 1, wherein a first position aperture of the at least one aperture of a given vertical support member of the pair of vertical support members extends in a generally horizontal direction across a portion of a width of the given vertical support member, wherein the pitch angle of the head position of the patient is adjustable by aligning the set of adjustment mechanisms at one of a series of possible positions along the first position aperture.

3. The adjustable cradle assembly of claim 2, wherein the first position aperture comprises a curved opening.

4. The adjustable cradle assembly of claim 1, wherein each vertical support member of the pair of vertical support members comprises two or more position apertures arranged at a vertical interval on the respective vertical support member.

5. The adjustable cradle assembly of claim 1, wherein the cradle includes at least one protrusion configured to pivotally mate with a corresponding aperture of the at least one vertical support member for setting the pitch angle.

6. The adjustable cradle assembly of claim 1, wherein each adjustment mechanism comprises a fiducial marker for identifying the pitch angle.

7. The adjustable cradle assembly of claim 1, further comprising a sensor to measure an angle of a head position of a patient relative to the platform.

8. The adjustable cradle assembly of claim 1, further comprising a set of attachment mechanisms configured to releasably lock the head fixation ring in the cradle at a fixed position.

9. The adjustable cradle assembly of claim 1, wherein the locking mechanism of the base comprises a set of securing locations configured to releasably receive a set of alignment mechanisms for detachably locking the base to the platform at a selected position.

10. The adjustable cradle assembly of claim 1, wherein the base comprises a pair of brackets such that the cradle spans between the pair of vertical support members of the base across a gap between the pair of brackets.

* * * * *